United States Patent [19]

Franzusoff

[11] Patent Number: 5,413,914
[45] Date of Patent: May 9, 1995

[54] YEAST ASSAY TO IDENTIFY INHIBITORS OF DIBASIC AMINO ACID PROCESSING ENDOPROTEASES

[75] Inventor: Alex Franzusoff, Boulder, Colo.

[73] Assignee: The Regents of the University of Colorado, Boulder, Colo.

[21] Appl. No.: 88,322

[22] Filed: Jul. 7, 1993

[51] Int. Cl.$^6$ .................. C12Q 1/37; C12Q 1/00; C12N 9/60
[52] U.S. Cl. ...................... 435/23; 435/7.9; 435/7.91; 435/224; 435/810; 435/975
[58] Field of Search ................ 435/23, 7.9, 7.91, 183, 435/219, 224, 810, 975

[56] References Cited

U.S. PATENT DOCUMENTS

| 4,929,553 | 5/1990 | Bussey | 435/172.3 |
| 5,162,220 | 11/1992 | Oshima | 435/224 |
| 5,234,830 | 8/1993 | Oshima | 435/252.3 |

FOREIGN PATENT DOCUMENTS 2024277 3/1991 Canada.

OTHER PUBLICATIONS

Angliker, H., The Synthesis of Inhibitors for . . . Biochemical Journal vol. 293 Part 1 Jul. 1, 1993. pp. 75–81.
Ashorn, Per et al., "An Inhibitor of the Protease Blocks Maturation of Human and Simian Immunodeficiency Viruses and Spread of Infection"; pp. 7472–7476, 1990, *Proc. Natl. Acad. Sci. USA*, vol. 87, Oct.
Baker, David et al., "Reconstitution of SEC Gene Product-Dependent Intercompartmental Protein Transport"; pp. 335–344, 1988, *Cell*, vol. 54, Jul.
Baldari, C. et al., "Plasmids pEMBLY: New Single-Stranded Shuttle Vectors for the Recovery and Analysis of Yeast DNA Sequence"; pp. 27–32, 1985, *Gene*, vol. 35.
Barr, Philip J., "Mammalian Subtilisins: The Long-Sought Dibasic Processing Endoproteases"; pp. 1–3, 1991, *Cell*, vol. 66, Jul.
Barr, Philip J. et al., "Expression and Processing of Biologically Active Fibroblast Growth Factors in the Yeast *Saccharomyces cerevisiae*"; pp. 16471–16478, 1988, *J. Biol. Chem.*, vol. 263, No. 31, Nov.
Barr, Philip J. et al., "cDNA and Gene Structure for a Human Subtilisin-Like Protease with Cleavage Specificity for Paired Basic Amino Acid Residues"; pp. 319–328, 1991, *DNA & Cell Biol.*, vol. 10, No. 5.
Bathurst, Ian C. et al., "Yeast KEX2 Protease Has the Properties of a Human Proalbumin Converting Enzyme"; pp. 348–350, 1987, *Science*, vol. 235, Jan.
Bathurst, Ian C. et al., "N Myristylatin of the Human Immunodeficiency Virus Type 1 gag Polyprotein Precursor in *Saccharomyces cerevisiae*"; pp. 3176–3179, 1989, *J. Virol.*, vol. 63, No. 7, Jul.
Berman, Phillip W. et al., "Expression of Membrane-Associated and Secreted Variants of gp160 of Human Immunodeficiency Virus Type 1 in Vitro and in Continuous Cell Lines"; pp. 3135–3142, 1988, *J. Virol.*, vol. 62, No. 9, Sep.
Bosch, Marnix L. et al., "Identification of the Fusion Peptide of Primate Immunodeficiency Viruses", pp. 694–697, 1989, *Science*, vol. 244, May.

(List continued on next page.)

Primary Examiner—Michael G. Wityshyn
Assistant Examiner—Ralph Gitomer
Attorney, Agent, or Firm—Sheridan Ross & McIntosh

[57] ABSTRACT

The present invention relates to a novel method to identify compounds that inhibit proteolytic cleavage by dibasic amino acid processing endoproteases that includes contacting a yeast strain with a putative inhibitory compound under conditions in which, in the absence of the compound, the yeast strain can cleave a precursor protein having a dibasic amino acid processing site and determining if the putative inhibitory compound inhibits cleavage of the precursor protein. The present invention includes a method to identify compounds capable of inhibiting infectious agents, such as viruses, that depend upon dibasic amino acid processing endoprotease cleavage for propagation. The present invention also includes assay kits based on such a method.

49 Claims, 1 Drawing Sheet

OTHER PUBLICATIONS

Bosch, Valerie et al., "Mutational Analysis of the Human Immunodeficieny Virus Type 1 *env* Gene Product Proteolytic Cleavage Site"; pp. 2337–2344, 1990, *J. Virol.*, vol. 64, No. 5, May.

Brake, Anthony J. et al., "α–Factor–Directed Synthesis and Sercretion of Mature Foregin Proteins in *Saccharomyces cerevisiae*, pp. 4642–4646, 1984, *Proc. Natl. Acad. Sci. USA*, vol. 81, Aug.

Brennan, Stephen O. et al., "Calcium–Dependent KEX-2–Like Protease Found in Hepatic Secretory Vesicles Converts Proalbumin to Albumin"; pp. 167–170, 1988, *FEBS Lett.*, vol. 229, No. 1, Feb.

Brenner, Charles et al., "Structural and Enzymatic Charactrization of a Purified Prohormone–Processing Enzyme: Secreted, Soluble Kex2 Protease"; pp. 922–926, 1992, *Proc. Natl. Acad. Sci. USA*, vol. 89, Feb.

Bresnahan, Patricia A. et al., "Human *fur* Gene Encodes a Yeast KEX2-like Endoprotease That Cleaves Pro–β–NGF In Vivo"; pp. 2851–2859, 1990, *J. Cell Biol.*, vol. 111, Dec.

Chan, Russell K. et al., "Extracellular Suppression Allows Mating by Pheromone–Deficient Sterile Mutants of *Saccharomyces cerevisiae*"; pp. 903–906, *J. Bacteriol*, vol. 155, No. 2, Aug.

Copeland, Constance S. et al., "Assembly of Influenza Hemagglutinin Trimers and Its Role in Intracellular Transport"; pp. 1179–1191, 1986, *J. Cell Biol.*, vol. 103, Oct.

Dewar, Robin L. et al., "Biosynthesis and Processing of Human Immunodeficiency Virus Type 1 Envelope Glycoproteins: Effects of Monensin on Glycosylatin and Transport"; pp. 2452–2456, 1989, *J. of Virol.*, vol. 63, No. 6, Jun.

Dreyer, Geoffrey B. et al., "Hydroxyethylene Isostere Inhibitors of Human Immunodeficiency Virus–1 Protease: Structure–Activity Analysis Using Enzyme Kinetics, X–ray Crystallography, and Infected T–Cell Assays"; pp. 6646–6659, 1992, *Biochem.*, vol. 31.

Dreyer, Geoffrey B. et al., "Inhibition of Human Immunodeficiency Virus 1 Protease in vitro: Rational Design of Substrate Analogue Inhibitors"; pp. 9752–9756, 1989, *Proc. Natl. Acad. Sci. USA*, vol. 86, Dec.

Earl, Patricia L. et al., "Biological and Immunological Properties of Human Immunodeficiency Virus Type 1 Envelope Glycoprotein: Analysis of Proteins with Truncations and Deletions Expressed by Recombinant Vaccinia Viruses"; pp. 31–41, 1991, *J. Virol.*, vol. 65, No. 1, Jan.

Earl, Patricia L. et al., "Folding, Interaction with GRP78–BiP, Assembly, and Transport of the Human Immunodeficiency Virus Type 1 Envelope Protein"; pp. 2047–2055, 1991, *J. Virol*, vol. 65, No. 4, Apr.

Egel–Michi, "A Novel Aspartyl Protease Allowing *KEX2*-Independent *M Fα* Propheromone Processing in *Yeast*", pp. 127–137, 1990, *Yeast*, vol. 6. (partly illegible)

Einfeld, David et al., "Oligomeric Structure of a Prototype Retrovirus Glycoprotein"; pp. 8688–8692, 1988, *Proc. Natl. Acad. Sci. USA*, vol. 85, Nov.

Fisher, Joseph M. et al., "Prohormone Processing and the Secretory Pathway"; pp. 16515–16518, 1988, *J. Biol. Chem.*, vol. 263, No. 32, Nov.

Fitting, Thomas et al., "Evidence for a Glycoprotein Signal Involved in Transport between Subcellular Organelles"; pp. 14011–14017, 1982, *J. Biol. Chem.*, vol. 257, No. 23, Dec.

Franzusoff, Alex, "Beauty and the Yeast: Compartmental Organization of the Secretory Pathway"; pp. 309–324, 1992, *Seminars Cell Biol.*, vol. 3.

Franzusoff, Alex et al., "Localization of Components Involved in Protein Transport and Processing Through the Yeast Golgi Apparatus"; pp. 27–37, 1991, *J. of Cell Biol.*, vol. 112, No. 1, Jan.

Franzusoff, Alex et al., "Functional Compartment of the Yeast Golgi Apparatus are Defined by the *sec7* Mutation"; pp. 2695–2702, 1989, *EMBO J.*, vol. 8, No. 9.

Freed, Eric O. et al., "A Mutation in the Human Immunodeficiency Virus Type 1 Transmembrane Glycoprotein gp41 Dominantly Interferes with Fusion and Infectivity"; pp. 70–74, 1992, *Proc. Natl. Acad. Sci. USA*, vol. 89, Jan.

Freed, Eric O. et al., "Characterization of the Fusion Domain of the Human Immunodeficiency Virus Type 1 Envelope Glycoprotein gP41"; pp. 4650–4654, 1990, *Proc. Natl. Acad. Sci. USA*, vol. 87, Jun.

Fuller, Robert S. et al., "Intracellular Targeting and Structural Conservation of a Prohormone-processing Endoprotease"; pp. 482–486, 1989, *Science*, vol. 246, Oct.

Fuller, Robert S. et al., "Yeast Prohormone Processing Enzyme (*KEX2*) Gene Product) is a $Ca^{2+}$–Dependent Serine Protease"; pp. 1434–1438, 1989, *Proc. Natl. Acad. Sci. USA*, vol. 86, Mar.

(List continued on next page.)

OTHER PUBLICATIONS

Garcia-Blanco, Mariano A., et al., "Molecular Basis of Latency in Pathogenic Human Viruses", pp. 815-820, 1991, *Science*, vol. 254, Nov.

Garten, Wolfgang et al., "Inhibition of Proteolytic Activation of Influenza Virus Hemagglutinin by Specific Peptidyl Chloroalkyl Ketones", pp. 25-31, 1989, *Virol.*, vol. 172.

Göttlinger, Heinrich G. et al., "Role of Capsid Precursor Processing and Myristoylation in Morphogenesis and Infectivity of Human Immunodeficiency Virus Type 1"; pp. 5781-5785, 1989, *Proc. Natl. Acad. Sci. USA*, vol. 86, Aug.

Grahm, Todd R. et al., "Compartmental Organization of Golgi-Specific Protein Modification and Vacuolar Protein Sorting Events Defined in a Yeast *sec18* (*NSF*) Mutant"; pp. 207-218, 1991, *J. Cell Biol.*, vol. 114, No. 2, Jul.

Guy, Bruno et al., "Specific Inhibitor of Cysteine Proteases Impairs a Vif-Dependent Modification of Human Immunodeficiency Virus Type 1 Env Protein"; pp. 1325-1331, 1991, *J. Virol.*, vol. 65, No. 3, Mar.

Haffar, Omar K. et al., "The Carboxy Terminus of Human Immunodeficiency Virus Type 1 gp160 Limits Its Proteolytic Processing and Transport in Transfected Cell Lines"; pp. 3100-3103, *J. Virol.*, vol. 64, No. 6, Jun.

Haseltine, William A., "Molecular Biology of the Human Immunodeficiency Virus Type 1"; pp. 2349-2360, 1991, *FASEB J.*, vol. 5, Jul.

Hatsuzawa, Kiyotaka et al., "Structure and Expression of Mouse Furin, a Yeast Kex2-Related Protease", pp. 22075-22078, 1990, *J. Biol. Chem.*, vol. 265, No. 36, Dec.

Hattori, Toshio et al., "Involvement of Tryptase-Related Cellular Proteases(s) in Human Immunodeficiency Virus Type 1 Infection", pp. 48-52, 1989, *FEBS Lett.*, vol. 248, No. 1, 2 May.

Hosaka, Masahiro et al., "Arg-X-Lys/Arg-Arg Motif as a Signal for Precursor Cleavage Catalyzed by Furin Within the Constitutive Secretory Pathway", pp. 12127-12130, 1991, *J. Biol. Chem.*, vol. 266, No. 19, Jul.

Inocencio, Noel M. et al., "A Mutant CHO-K1 Strain with Resistance to *Pseudomonas* Exotoxin A is Unable to Process the Precursor Fusion Glycoprotein of Newcastle Disease Virus", pp. 593-595, 1993, *J. Virol.*, vol. 67, No. 1, Jan.

Johnston, Margaret I. et al., "Present Status and Future Prospects for HIV Therapies", pp. 1286-1293, 1993, *Science*, vol. 260, May.

Julius, David et al., "Yeast α Factor is Processed from a Larger Precursor Polypeptide: The Essential Role of a Membrane-Bound Dipeptidyl Aminopeptidase", pp. 839-852, 1983, *Cell*, vol. 32, Mar.

Julius, David et al., "Isolation of the Putative Structural Gene for the Lysine-Arginine-Cleaving Endopeptidase Required for Processing of Yeast Prepro-α-Factor", pp. 1075-1089, 1984, *Cell*, vol. 37.

Keränen, Sirkka, "Synthesis and Processing of Semliki Forest Virus Polyprotein in *Saccharomyces cerevisiae*: a Yeast Type Glycosylation of E1 Envelope Protein", pp. 267-275, 1986, *Gene*, vol. 48.

Kiefer, Michael C. et al., "Identification of a Second Human Subtilisin-Like Protease Gene in the *fes/fps* Region of Chromosome 15", pp. 757-769, 1991, *DNA and Cell Biol.*, vol. 10, No. 10.

Kowalski, Mark et al., "Attenuation of Human Immunodeficiency Virus Type 1 Cytopathic Effect by a Mutation Affecting the Transmembrane Envelope Glycoprotein", pp. 281-291, 1991, *Virol.*, vol. 65, No. 1, Jan. Mutation Affecting the Transmember Envelope Glycoprotein", pp. 281-291, 1991, *Virol.*, vol. 65, No. 1, Jan.

Kowalski, Mark et al., "Functional Regions of the Envelope Glycoprotein of Human Immunodeficiency Virus Type 1", pp. 1351-1355, 1987, *Science*, vol. 237, Sep.

Kozarsky, Karen et al., "Glycosylation and Processing of the Human Human Immunodeficiency Virus Type 1 Envelope Protein", pp. 163-169, 1989, *J. Acq. Immun. Def. Syn.*, vol. 2, No. 2.

Kramer, R. A. et al., "HTLV-III *gag* Protein is Processed in Yeast Cells by the Virus pol-Protease", pp. 1580-1584, 1986, *Science*, vol. 231, Mar.

Kuroda, Shun'ichi et al., "Hepatitis B Virus Envelope L Protein Particles", pp. 1953-1961, *J. Biol. Chem.*, vol. 267, No. 3, Jan.

Kwang, Hwei-Sing et al., "Simian Retrovirus-D Serotype 1 (SRV-1) Envelope Glycoproteins gp70 and gp20: Expression in Yeast Cells and Identification of Specific Antibodies in Sera from Monkeys that Recovered from SRV-1 Infection", pp. 1774-1780, 1988, *J. Virol.*, vol. 62, No. 5, May.

(List continued on next page.)

OTHER PUBLICATIONS

Lapatto, Risto et al., "X-Ray Analysis of HIV-1 Proteinase at 2.7Å Resolution Confirms Structural Homology Among Retroviral Enzymes", pp. 299–302, 1989, *Nature*, vol. 342, Nov.

Legrain, Michèle et al., "Biochemical and Immunological Characterization of the Bovine Leukemia Virus (BLV) Envelope Glycoprotein (gp51) produced in *Saccharomyces cerevisiae*", pp. 227–237, 1989, *Gene*, vol. 79.

Leibowitz, Michael J. et al., "A Chromosomal Gene Required for Killer Plasmid Expression, Mating and Spore Maturation in *Saccharomyces cerevisiae*", pp. 2061–2065, 1976, *Proc. Natl. Acad. Sci. USA*, vol. 73, No. 6, Jun.

Machida, Curtis A. et al., "Role of Partial Proteolysis in Processing Murine Leukemia Virus Membrane Envelope Glycoproteins to the Cell Surface", pp. 14018–14022, 1982, *J. Biol. Chem.*, vol. 257, No. 23, Dec.

Manetta, Joseph V. et al., "Design and Implementation of a Particle Concentration Fluorescence Method for the Detection of HIV-1 Protease Inhibitors", pp. 10–15, 1992, *Anal. Biochem.*, vol. 202.

Matayoshi, Edmund, D. et al., "Novel Fluorogenic Substrates for Assaying Retroviral Proteases by Resonance Energy Transfer", pp. 954–958, 1990, *Science*, vol. 247, Feb.

McCune, Joseph M. et al., "Endoproteolytic Cleavage of gp160 is Required for the Activation of Human Immunodeficiency Virus", pp. 55–67, 1988, *Cell*, vol. 53, Apr.

Meek, Thomas D. et al., "Inhibition of HIV-1 Protease in Infected T-Lymphocytes by Synthetic Peptide Analogues", pp. 90–92, 1990, *Nature*, vol. 343, Jan.

Miller, Maria et al., "Structure of Complex of Synthetic HIV-1 Protease with a Substrate-Based Inhibitor at 2.3Å Resolution", pp. 1149–1152, 1989, *Science*, vol. 246, Dec.

Mitsuya, Hiroaki et al., "Molecular Targets for AIDS Therapy", pp. 1533–1544, 1990, *Science*, vol. 249, Sep.

Mitsuya, Hiroaki et al., "Targeted Therapy of Human Immunodeficiency Virus-Related Disease", pp. 2369–2380, 1991, *FASEB J.*, vol. 5, Jul.

Mizuno, Kensaku et al., "A Unique Membrane-Bound, Calcium-Dependent Endopeptidase with Specificity Toward Paired Basic Residues in Rat Liver Golgi Fractions", pp. 780–787, 1989, *Biochem. Biophys. Res. Comm.*, vol. 164, No. 2, Oct.

Mizuno, Kensaku et al., "Yeast KEX2 Gene Encodes and Endopeptidase Homologous to Subtilisin-Like Serine Proteases", pp. 246–254, 1988, *Biochem Biophys. Res. Comm.*, vol. 156, No. 1, Oct.

Moehring, Joan M. et al., "Expression of Mouse Furin in a Chinese Hamster Cell Resistant to *Pseudomonas* Exotoxin A and Viruses Complements the Genetic Lesion", pp. 2590–2594, 1993, *J. Biol. Chem.*, vol. 268, No. 4, Feb.

Montefiori, David C. et al., "Role of Protein N-Glycosylation in Pathogenesis of Human Immunodeficiency Virus Type 1", pp. 9248–9252, 1988, *Proc. Natl. Acad. Sci. USA*, vol. 85, Dec.

Morrison, T. et al., "Intracellular Processing of the Newcastle Disease Virus Fusion Glycoprotein", pp. 851–857, 1985, *J. Virol.*, vol. 53, No. 3, Mar.

Nara, P. L. et al., "Quantitative Infectivity Assay for HIV-1 and HIV-2", pp. 469–470, 1988, *Nature*, vol. 332, Mar.

Navia, Manuel A. et al., "Three-dimensional Structure of Aspartyle Protease from Human Immunodeficiency Virus HIV-1", pp. 615–620, 1989, *Nature*, vol. 337, Feb.

Oda, Kimimitsu, "Sequence Requirements for Proteolytic Cleavage Precursors with Paired Basic Amino Acids", pp. 1181–1186, 1991, *Biochem. Biophys. Res. Comm.*, vol. 179, No. 3, Sep.

Owens, R. A., "The Rapid Identification of HIV Protease Inhibitors Through the Synthesis and Screening of Defined Peptide Mixtures", pp. 402–408, 1991, *Biochem. Biophys. Res. Comm.*, vol. 181, No. 1, Nov.

Perez, Lautaro G. et al., "Mutants of the Rous Sarcoma Virus Envelope Glycoprotein that Lack the Transmembrane Anchor and Cytoplasmic Domains: Analysis of Intracellular Transport and Assembly into Virions", pp. 2981–2988, 1987, *J. Virol.*, vol. 61, No. 10, Oct.

Perez, Lautaro G. et al., "Mutations within the Proteolytic Cleavage Site of the Rous Sarcoma Virus Glycoprotein that Block Processing to gp85 and gp37", pp. 1609–1614, 1987, *J. Virol.*, vol. 61, No. 5, May.

Pichuantes, Sergio et al., "Recombinant HIV2 Protease Processes HIV 1 Pr53$^{gag}$ and Analogous Junction Peptides in Vitro", pp. 13890–12898, 1990, *J. Biol. Chem.*, vol. 265, No. 23, Aug.

Pichuantes, Sergio et al., "Expression of Heterologous (List continued on next page.)

OTHER PUBLICATIONS

Gene Products in Yeast", Chapter 8 in *Principles and Practice of Protein Engineering*, in press, 1993 (J. L. Cleland & C. Craik, eds.), Hauser Publ.

Pinter, Abraham et al., "Oligomeric Structure of gp41, the Transmembrane Protein of Human Immunodeficiency Virus Type 1", pp. 2674-2679, 1989, *J. Virol.*, vol. 63, No. 6, Jun.

Pique, Claudine et al., "Human T-Cell Leukemia Virus Type 1 Envelope Protein Maturation Process: Requirements for Syncytium Formation", pp. 906-913, 1992, *J. Virol.*, vol. 66, No. 2, Feb.

Renneisen, Karin et al., "Inhibition of Expression of Human Immunodeficiency Virus-1 in Vitro by Antibody-Targeted Liposomes Containing Antisense RNA to the *env* Region", pp. 16337-16342, 1990, *J. Biol. Chem.*, vol. 265, No. 27, Sep.

Roberts, Noel A. et al., "Rational Design of Peptide-Based HIV Proteinase Inhibitors", pp. 358-361, 1990, *Science*, vol. 248, Apr.

Robey, W. Gerard et al. "Charactrization of Envelope and Core Structural Gene Products of HTLV-III with Sera from AIDS Patients", pp. 593-595, 1985, *Science*, vol. 228, May.

Sanchez-Pescador, Ray et al., "Nucleotide Sequence and Expression of an AIDS-Associated Retrovirus (ARV-2)", pp. 484-492, 1985, *Science*, vol. 227, Feb.

Scheid, Andreas et al., "Identification of Biological Activities of Paramyxovirus Glycoproteins. Activation of Cell Fusion, Hemolysis, and Infectivity by Proteolytic Cleavage of an Inactive Precursor Protein of Sendai Virus", pp. 475-490, 1974, *Virol.*, vol. 57.

Scheid, Andreas et al., "Protease Activation Mutants of Sendai Virus", pp. 265-277, 1976, *Virol.*, vol. 69.

Seidah, N. G. et al., "cDNA Sequence of Two Distinct Pituitary Proteins Homologous to Kex2 and Furin Gene Products: Tissue Specific mRNAs Encoding Candidates for Pro-Hormone Processing Proteinases", pp. 415-424, 1990, *DNA and Cell Biol.*, vol. 9, No. 6.

Shen, Shi-Hsiang et al., "Synthesis and Secretion of Hepatitis B Middle Surface Antigen by the Methylotrophic Yeast *Hansenula polymorpha*", pp. 303-309, 1989, *Gene*, vol. 84.

Smeekens, Steven P. et al., "Identification of a cDNA Encoding a Second Putative Prohormone Convertase Related to PC2 in AtT20 Cells and Islets of Langerhans", pp. 340-344, 1991, *Proc. Natl. Acad. Sci. USA*, vol. 88, Jan.

Smeekens, Steven P. et al., "Identification of a Human Insulinoma cDNA Encoding a Novel Mammalian Protein Structurally Related to the Yeast Dibasic Processing Protease Kex2", pp. 2997-3000, 1990, *J. Biol. Chem.*, vol. 265, No. 6, Feb.

Sodroski, Joseph et al., "Role of the HTLV-III/LAV Envelope in Syncytium Formation and Cytopathicity", pp. 470-474, 1986, *Nature*, vol. 322, Jul.

Starcich et al., "Identification and Characterization of Conserved and Variable Regions in the Envelope Gene of HTLV-III/LAV, the Retrovirus of AIDS", pp. 637-648, 1986, *Cell*, vol. 45, Jun.

Stein, Barry S. et al., "Intracellular Processing of the gp160 HIV-1 Envelope Precursor", pp. 2640-2649, 1990, *J. Biol. Chem.*, vol. 265, No. 5, Feb.

Stieneke-Gröber, Andrea et al., "Influenza Virus Hemagglutinin with Multibasic Cleavage Site is Activated by Furin, a Subtilisin-Like Endoprotease", pp. 2407-2414, 1992, *EMBO J.*, vol. 11, No. 7.

Stevenson, M. et al., "Cloning and Characterization of Human Immunodeficiency Virus Type 1 Variants Diminished in the Ability to Induce Syncytium-Independent Cytolysis", pp. 3792-3803, 1990, *J. Virol.*, vol. 64, No. 8, Aug.

Thim, Lars et al., "Secretion and Processing of Insulin Precursors in Yeast", pp. 6766-6770, 1986, *Proc. Natl. Acad. Sci. USA*, vol. 83, Sep.

Thomas, Gary et al., "Yeast *KEX2* Endopeptides Correctly Cleaves a Neuroendocrine Prohomone in Mammalian Cells", pp. 226-229, 1988, *Science*, vol. 241, Jul.

Valenzuela, Pablo et al., "Synthesis and Assembly of Hepatitis B Virus Surface Antigen Particles in Yeast", pp. 347-350, 1982, *Nature*, vol. 298, Jul.

Veronese, Fulvia D. et al., "Characterization of gp41 as the Transmembrane Protein Coded by the HTLV-III/LAV Envelope Gene", pp. 1402-1405, 1985, *Science*, vol. 229, Sep.

Vonèche, V. et al., "Fusogenic Segments of Bovine Leukemia Virus and Simian Immunodeficiency Virus are Interchangeable and Mediate Fusion by Means of Oblique Insertion in the Lipid Bilayer of Their Target Cells", pp. 3810-3814, 1992, *Proc. Natl. Acad. Sci. USA*, vol. 89, May.

Walker, Bruce D. et al., "Inhibition of Human Im-
(List continued on next page.)

OTHER PUBLICATIONS munodeficiency Virus Syncytiumn Formation and Virus Replication by Castanospermine", pp. 8120–8124, 1987, *Proc. Natl. Acad. Sci. USA*, vol. 84, Nov.

Wen, Duanzhi et al., "Expression of Genes Encoding Vesicular Stomatitis and Sindbis Virus Glycoproteins in Yeast Leads to Formation of Disulfide–Linked Oligomers", pp. 150–154, 1986, *Virol.*, vol. 153.

Wen, Duanzhi et al., "Regulated Expression of Sindbis and Vesicular Stomatitis Virus Glycoproteins in *Saccharomyces cerevisiae*", pp. 3639–3643, 1986, *Proc. Natl. Acad. Sci. USA*, vol. 83, Jun.

Wickner et al, "Two Chromosomal Genes Required for Killing Expression in Killer Strains of *Saccharomyces cerevisiae*", pp. 429–442, 1976, *Genetics*, vol. 82, Mar.

Wilcox, Celeste A. et al., "Posttranslational Processing of the Prohomone–Cleaving Kex2 protease in the *Saccharomyces cerevisiae* Secretory Pathway", pp. 297–307, 1991, *J. Cell Biol.*, vol. 115, No. 2, Oct.

Willey, Ronald L. et al., "Biosynthesis, Cleavage, and Degradation of the Human Immunodeficiency Virus 1 Envelope Glycoprotein gp160", pp. 9580–9584, 1988, *Proc. Natl. Acad. Sci. USA*, No. 85, Dec.

Willis, John W. et al., "Mutations of the Rous Sarcoma Virus *env* Gene that Affect the Transport and Subcellular Location of the Glycoprotein Products", pp. 2011–2023, 1984, *J. Cell Biol.*, vol. 99, Dec.

Wise, Robert J. et al., "Expressin of a Human Proprotein Processing Enzyme: Correct Cleavage of the von Willebrand Factor Precursor at a Paired Basic Amino Acid Site", pp. 9378–9382, 1990, *Proc. Natl. Acad. Sci. USA*, vol. 87, Dec.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:1:

Lys  Xaa  Xaa  Lys
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:2:

Lys  Xaa  Xaa  Arg
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:3:

Arg  Xaa  Xaa  Lys
    1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:4:

Arg  Xaa  Xaa  Arg
    1

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:5:

Arg  Glu  Lys  Arg
    1

( 2 ) INFORMATION FOR SEQ ID NO:6:

-continued (i) SEQUENCE CHARACTERISTICS:
    (A) LENGTH: 10 amino acids
    (B) TYPE: amino acid
    (D) TOPOLOGY: unknown (ii) MOLECULE TYPE: peptide (xi) SEQUENCE DESCRIPTION: SEQ ID NO:6:

Arg Pro Lys Gln Gln Phe Phe Gly Leu Met
1               5                   10

YEAST ASSAY TO IDENTIFY INHIBITORS OF DIBASIC AMINO ACID PROCESSING ENDOPROTEASES

FIELD OF THE INVENTION

The present invention relates to a yeast-based assay to identify compounds that inhibit dibasic amino acid processing endoproteases. Such compounds can be used, for example, to treat infectious diseases in which dibasic amino acid processing endoprotease cleavage is involved in disease progression. In particular, the assay can be used to identify antiviral drugs, including drugs that reduce the spread of HIV and that retard or reverse the onset of the acquired immunodeficiency syndrome (AIDS). The present invention is also related to a method to isolate dibasic amino acid processing endoprotease genes.

BACKGROUND OF THE INVENTION

A number of enveloped viruses, including retroviruses, hepatitis viruses, herpes viruses, orthomyxoviruses and paramyxoviruses, produce precursor envelope glycoproteins that require cleavage by a cellular dibasic amino acid processing endoprotease as one step in the process of envelope glycoprotein maturation. As precursor envelope glycoproteins are being synthesized, they are directed into the host cell secretory pathway for transport to the cell surface. As the precursor proteins move through the pathway, they are subjected to a variety of post-translational events including glycosylation and proteolytic cleavage (see, for example, Stein et al., pp. 2640-2649, 1990, *J. Biol. Chem.*, vol. 265). The precursor human immunodeficiency virus (HIV) envelope protein gp160, for example, is co-translationally glycosylated and subsequently cleaved into gp120 and gp41 by a cellular dibasic amino acid processing endoprotease that apparently is localized in the Golgi apparatus. The gp120 and gp41 proteins are further glycosylated prior to reaching the infected cell surface. Cleavage of the HIV gp160 protein has been shown to be necessary for membrane fusion, syncytium formation and viral infectivity (see, for example, McCune et al., pp. 55-67, 1988, *Cell*, vol. 53; Kowalski et al., pp. 1351-1355, 1987, *Science*, vol. 237). The inventor, however, is unaware of antiviral drugs that have been designed to block cleavage of precursor envelope proteins by cellular dibasic amino acid processing endoproteases. Although the genes encoding human furin (also called PACE), murine furin, murine PC1 (also called PC3), human PC2, human PACE4, and human PACE 4.1 dibasic amino acid processing endoproteases have been isolated (for reviews, see Barr, pp. 1-3, 1991, *Cell*, vol. 66; Kiefer et al., pp. 757-769, 1991, *DNA and Cell Biology*, vol. 10), a number of cellular dibasic amino acid processing endoproteases remain to be identified, including the human CD4+ T-lymphocyte dibasic amino acid processing endoprotease responsible for cleaving HIV gp160 into gp120 and gp41.

Nucleoside analogs are a common type of antiviral drug, particularly for treating retroviral infections as the analogs can inhibit the ability of the retroviral reverse transcriptase enzyme to make a DNA copy of the incoming viral RNA. For example, HIV infections are being treated with AZT (3'-azidothymidine), ddI (2'3'-dideoxyinosine), ddC (2'3'-dideoxycytidine), and d4T (didehydrothymidine). Nucleoside analogs, however, have short half-lives and can exhibit substantial side effects. In addition, viruses resistant to the nucleoside analog being administered often develop within a relatively short period of time.

Non-nucleoside inhibitors of HIV reverse transcriptase, such as TIBO (tetrahydro-imidazo(4,5,1-jk)(1,4)-benzodiazepin-2(1H)-one), BI-RG-587 (11-cyclopropyl-7-methyl-dipyrido-(2,3-b:3'3'-f)1,4-diazepin-6H-5-one), pyridones, and bis(heteroaryl)piperazines, are also being developed and tested. Since these compounds are highly selective for the HIV reverse transcriptase enzyme, they apparently cause less severe side effects than do nucleoside analogs. Decreased sensitivity of HIV to these agents, however, develops rapidly.

The HIV-encoded aspartyl protease that processes the gag and gag/pol polyproteins to yield the mature structural proteins and enzymes required for virion formation (p24, p17, p15, reverse transcriptase) has also been targeted as an enzyme against which to design antiviral agents. HIV protease inhibitors, at least theoretically, can inhibit HIV production by chronically infected cells and, as such, have an advantage over reverse transcriptase inhibitors that apparently can only block replication if added to cells before HIV infection. Peptide-based substrate analogs are being prepared and tested. One drawback of HIV protease inhibitors is the development of HIV strains that are resistant to the inhibitor being administered.

Other strategies for inhibiting HIV infection that are being pursued include inhibition of other HIV-encoded proteins such as Tat, Rev, and integrase; blocking entry of the virus into the cell by, for example, soluble CD4 receptor molecules; targeted delivery of toxins to HIV-infected cells; inhibition of viral functions using antisense technology; and immune constitution protocols. Although several of these technologies are at the early stages of development, clinical trials conducted using some of these technologies have been disappointing. For a recent review of present and future strategies to treat HIV infection, see Johnston et al., pp. 1286-1293, 1993, *Science*, vol. 260.

Most assays used to test antiviral drugs are either in vitro or mammalian cell culture assays, many relying on the use of infectious virus. Mammalian cell culture assays are usually costly, complex, time-consuming, and potentially dangerous if infectious virus is used. Recently, a Drosophila cell-based assay was developed for screening inhibitors of the HIV Rev protein. For a review of methods to identify HIV inhibitors, see Johnston et al., 1993, *Science*, ibid.

Thus, there remains a need to identify antiviral drugs with improved efficacy that have fewer side effects than known drugs and against which an infected host is less likely to develop resistance. A preferred class of inhibitors to identify are those that can be used to treat infectious diseases, such as HIV infections, in which proliferation of the infectious agent depends on dibasic amino acid processing endoprotease cleavage. In order to identify such drugs in a rapid and straightforward manner, an improved assay is required that is less complex, less expensive, less time-consuming, and more selective than currently used methods. There is also a need for a method to identify the cellular dibasic amino acid processing endoproteases that effect cleavage of such infectious agents in vivo, such as the human CD4+ T-lymphocyte dibasic amino acid processing endoprotease that cleaves HIV gp160, in order to identify specific

SUMMARY OF THE INVENTION

The inventor has discovered that yeast strains having a functional Kex2 endoprotease are also able to properly process precursor proteins of other organisms (i.e., heterologous precursor proteins), such as mammalian precursor proteins, that require cleavage by a dibasic amino acid processing endoprotease in order to become mature proteins. Based on this finding, the present invention involves the use of yeast strains to identify compounds that inhibit a dibasic amino acid processing endoprotease from cleaving a heterologous precursor protein into one or more cleavage proteins. Such inhibitory compounds can reduce the infectivity of an infectious agent by interfering with the production of one or more cleavage proteins required in the production of an infectious agent. For example, many if not all envelope (or enveloped) viruses produce precursor envelope proteins that require cleavage by dibasic amino acid processing endoproteases in order to propagate infectious virus. One such precursor envelope protein is the HIV gp160. The present invention includes the use of a yeast-based assay to identify drugs capable of reducing the spread of HIV and, thus to retard or reverse the onset of AIDS, because the drugs are capable of blocking the cleavage of gp160 into gp120 and gp41 in T lymphocytes.

Furthermore, in light of the aforementioned discovery, yeast strains lacking a functional Kex2 endoprotease can be used to identify genes encoding other dibasic amino acid processing endoproteases that cleave specific precursor proteins in vivo. One example of such an endoprotease is the human CD4+ T-lymphocyte endoprotease(s) responsible for cleaving the precursor HIV envelope protein gp160 into the mature gp120 and gp41 glycoproteins, a cleavage that is required to form infectious virus and to promote fusion between HIV-infected and non-infected cells leading to immunodeficiency.

One embodiment of the present invention is a method to identify a compound that inhibits proteolytic cleavage by a dibasic amino acid processing endoprotease that includes the steps of (a) contacting a yeast strain with a putative inhibitory compound under conditions in which, in the absence of the compound, the yeast strain is capable of cleaving a precursor protein having a dibasic amino acid processing site and (b) determining if the putative inhibitory compound inhibits cleavage of the precursor protein. A number of yeast strains can be used, including *Saccharomyces cerevisiae*.

Cleavage can be monitored in a yeast strain that produces an active Kex2 endoprotease, or functional equivalent thereof. Alternatively, cleavage can be monitored in a Kex2 endoprotease-deficient yeast strain that can express a heterologous dibasic amino acid processing endoprotease, such as an animal or plant dibasic amino acid processing endoprotease (yeast Kex2 endoprotease-deficient yeast strains are viable as are Chinese hamster ovary cells that lack a functional dibasic amino acid processing endoprotease). Preferably the dibasic amino acid processing endoprotease is capable of effecting cleavage of at least one envelope protein of an enveloped virus. Precursor proteins can be either yeast precursor proteins or precursor proteins that are heterologous to the yeast strain that produces them. Preferred heterologous precursor proteins are proteins that when cleaved promote the propagation and/or infectivity of an infectious agent, such as the precursor envelope proteins of retroviruses and other enveloped viruses. Heterologous precursor proteins can include protein segments that enhance correct export and processing of the precursor protein. Putative inhibitory compounds can include peptides, mimetopes, and mixtures thereof. Cleavage inhibition can be detected using a variety of techniques including, for example, the α-factor zone clearing, or halo, assay.

Another embodiment of the present invention is a method to identify an inhibitory compound that reduces the infectivity of an infectious agent that includes the steps of (a) contacting a yeast strain with a putative inhibitory compound under conditions in which, in the absence of the compound, the yeast strain is capable of cleaving a precursor protein having a dibasic amino acid processing site and (b) determining if the putative inhibitory compound inhibits cleavage of the precursor protein. The ability of the compound to inhibit cleavage is indicative of (i.e., positively correlates with) the ability of the compound to reduce the spread of the infectious agent in an organism infected by the infectious agent.

Yet another embodiment of the present invention is a method to identify a compound capable of inhibiting an animal or plant dibasic amino acid processing endoprotease that includes (a) contacting a putative inhibitory compound with a secreted soluble dibasic amino acid processing endoprotease protein fragment in the presence of a precursor protein and (b) determining if the putative inhibitory compound is capable of inhibiting cleavage of the precursor protein by the protein fragment. The protein fragment can be a secreted soluble yeast Kex2 protein fragment or a soluble secreted fragment of an animal or plant dibasic amino acid processing endoprotease.

One embodiment of the present invention is a test kit to identify a compound capable of inhibiting a dibasic amino acid processing endoprotease that includes a yeast strain that is capable both of producing a yeast or heterologous precursor protein and of cleaving the precursor protein. The kit also includes a means for determining the extent of cleavage by the yeast strain in the presence of a putative inhibitory compound.

The present invention also includes yeast strains capable of producing a heterologous precursor protein having a dibasic amino acid processing site that are capable of correctly processing the precursor protein into at least one cleavage protein. Such strains include Kex2 endoprotease-deficient yeast strains capable of producing a heterologous dibasic amino acid processing endoprotease capable of cleaving the precursor protein. Particularly preferred yeast strains are of the species *Saccharomyces cerevisiae*.

Additional yeast strains of the present invention include Kex2 endoprotease-deficient yeast strains capable of producing a heterologous precursor protein but that are essentially incapable of correctly processing the precursor protein into at least one cleavage protein, such as *Saccharomyces cerevisiae* kex2Δ and progeny and mutants thereof, that are Kex2 endoprotease-deficient.

Another embodiment of the present invention includes compounds that inhibit dibasic amino acid processing endoproteases. Such compounds can be identified according to the heretofore disclosed methods and/or by using the heretofore disclosed test kits and/or yeast strains. Particularly useful inhibitory compounds of the present invention are compounds that are capable of inhibiting dibasic amino acid processing endoprotease cleavage of a precursor protein into at least one cleavage protein by at least about 50 percent when the compound is contacted with the endoprotease at a compound concentration of less than or about 100 micromolar, such that treatment with the inhibitory compound reduces the infectivity of an infectious agent, such as of a virus. Inhibitory compounds of the present invention can include a component that targets the compound to the desired cell type. Inhibitory compounds preferably enter cells by endocytosis.

Yet another embodiment of the present invention is a method to identify a gene encoding an animal or plant dibasic amino acid processing endoprotease that includes (a) transforming a Kex2 endoprotease-deficient yeast strain with a cDNA library prepared from RNA isolated from a cell type capable of producing the dibasic amino acid processing endoprotease; (b) isolating a transformed yeast strain capable of expressing a functional dibasic amino acid processing endoprotease as determined by the ability of the transformed yeast strain to form a clear zone, or halo, in an α-factor zone-clearing assay; and (c) recovering a cDNA encoding the dibasic amino acid processing endoprotease from the isolated transformed yeast strain.

DETAILED DESCRIPTION OF THE INVENTION

Figure 1:
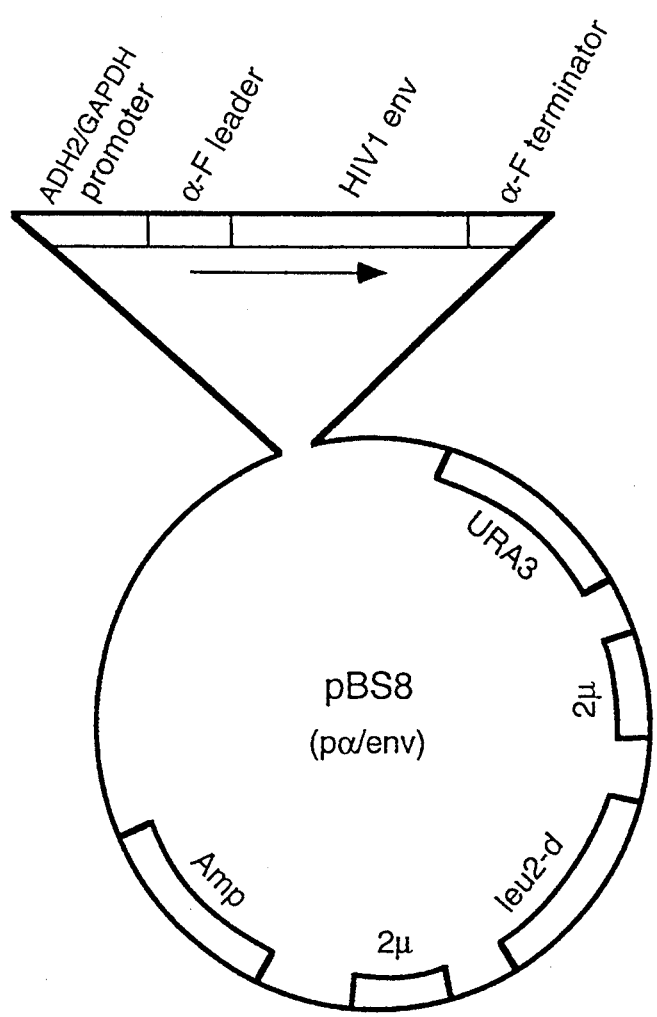
FIG. 1 is a schematic representation of recombinant molecule pα/env.

The present invention includes a novel method to identify compounds that inhibit dibasic amino acid processing endoproteases, yeast strains that are useful in such a method, and assay kits based on such a method. The present invention can also be used to isolate dibasic amino acid processing endoprotease genes.

The present invention includes the use of yeast strain assay systems, and particularly the use of the protein secretory apparatus of yeast, to identify compounds that inhibit a variety of organisms' dibasic amino acid processing endoproteases. Yeast strains possess a dibasic amino acid processing endoprotease located in the Golgi apparatus called Kex2 endoprotease (see, for example, Julius et al. pp. 1075–1089, 1984, *Cell*, vol. 37). Kex2 endoprotease is capable of processing (i.e., cleaving) yeast precursor proteins having dibasic amino acid processing sites, such as precursor proteins for α-factor mating pheromones and killer toxins. Yeast strains lacking a functional Kex2 endoprotease can grow normally; such strains, however, are unable to mate and show reduced functions at low growth temperatures (i.e., at less than about 14° C.). Apparently all wild-type yeast strains, regardless of genus or species, have a Kex2 endoprotease, or functional equivalent thereof, since all wild-type yeast strains apparently are capable of mating. As used herein, a functional equivalent of a Kex2 endoprotease is a yeast dibasic amino acid processing endoprotease that has a similar proteolytic activity to Kex2 and, as such, can produce, for example, mature α-factor mating pheromones. As used herein, the phrases a "yeast strain lacking a functional Kex2 endoprotease" and a "Kex2 endoprotease-deficient yeast strain" each refer to a yeast strain in which the Kex2 endoprotease is either absent or modified such that the enzyme has essentially no proteolytic activity (i.e., less than about 10 percent, preferably less than about 5 percent, and more preferably less than about 1 percent of wild-type Kex2 endoprotease activity). As such, a Kex2 endoprotease-deficient strain is essentially unable to produce mature α-factor mating pheromones unless the strain is supplemented with a functional dibasic amino acid processing endoprotease, for example, by transforming the strain with a gene encoding a functional dibasic amino acid processing endoprotease.

One embodiment of the present invention is a method to identify a compound that inhibits a dibasic amino acid processing endoprotease from cleaving a precursor protein heterologous to a yeast precursor protein that includes the steps of (a) contacting a yeast strain with a putative inhibitory compound under conditions in which, in the absence of the compound, the yeast strain is able to cleave either a yeast or heterologous precursor protein having a dibasic amino acid processing site, and (b) determining whether the putative inhibitory compound inhibits the ability of the yeast strain to cleave such a yeast or heterologous precursor protein. In the instance of a system based on cleavage of a yeast precursor protein, the ability of the putative inhibitory compound to inhibit the cleavage of the yeast precursor protein is indicative of (positively correlates with) the ability of the putative inhibitory compound to inhibit the cleavage of a heterologous precursor protein. Such a correlation is based on the finding that yeast Kex2 endoproteases are capable of cleaving heterologous precursor proteins. Since yeast Kex2 endoproteases can cleave heterologous precursor proteins naturally cleaved by other dibasic amino acid processing endoproteases, albeit possibly not with equivalent affinity or specific activity, it has been found that compounds that inhibit Kex2 endoprotease can inhibit heterologous dibasic amino acid processing endoproteases. The heterologous precursor protein is preferably a protein, the cleavage of which is instrumental in the formation of an infectious agent and, as such, inhibition of the cleavage reduces the infectivity of such an agent.

According to the aforementioned method, cleavage of the yeast or heterologous precursor protein can be accomplished by the yeast strain's endogenous Kex2 endoprotease or functional equivalent thereof. An advantage of using a yeast strain expressing its own Kex2 endoprotease is the ability to easily screen a number of compounds for potential dibasic amino acid processing endoprotease inhibitory activity. Alternatively, a yeast strain lacking a functional yeast Kex2 endoprotease (i.e., a Kex2 endoprotease-deficient yeast strain), can be transformed with a gene encoding a heterologous dibasic amino acid processing endoprotease in such a manner that the yeast strain is able to produce (i.e., express) the heterologous dibasic amino acid processing endoprotease. Preferably, the heterologous dibasic amino acid processing endoprotease is the protease that naturally cleaves the heterologous precursor protein. An advantage of using a Kex2 endoprotease-deficient strain expressing a heterologous dibasic amino acid processing endoprotease is that such a method identifies compounds that interact with the heterologous dibasic amino acid processing endoprotease with high affinity and specificity without affecting cell viability. A preferred yeast strain to use to identify compounds that inhibit HIV infection is a Kex2 endoprotease-deficient *Saccharomyces cerevisiae* strain that expresses a human CD4+ T-lymphocyte dibasic amino acid processing endoprotease responsible for cleaving an HIV gp160, such as HIV-1 gp160, HIV-2 gp160, or functional equivalents thereof.

The term dibasic amino acid processing endoprotease refers to any proteolytic enzyme that cleaves a precursor protein (also referred to as a proprotein) at a dibasic amino acid processing site within the precursor protein. Dibasic amino acid processing endoproteases are typically serine proteases of the subtilisin family, such as those described by Barr, pp. 1–3, 1991, *Cell,* Vol. 66. Dibasic amino acid processing endoproteases of the present invention can be of any species, including viral, bacterial, fungal, plant, and animal dibasic amino acid processing endoproteases.

Preferred dibasic amino acid processing endoproteases are cellular dibasic amino acid processing endoproteases that cleave precursor proteins into cleavage proteins that enable the propagation of an infectious agent. Cellular dibasic amino acid processing endoproteases are preferred over enzyme targets inherent to the infectious agent (e.g., polymerases, regulatory factors, surface antigens, or proteases encoded by the infectious agent) because it is believed that over time, drug-resistant infectious agents are likely to develop much more rapidly than are drug-resistant cellular proteases. Cellular dibasic amino acid processing endoproteases are also attractive targets for inhibitory drug therapy because the cellular location of dibasic amino acid processing endoproteases in the secretory pathway (often in or near the Golgi apparatus) causes dibasic amino acid processing endoproteases to be susceptible to compounds that are endocytosed by cells. As such, inhibitory drug compounds can be of any substance capable of being endocytosed including compounds that are at least partially, and preferably essentially completely, soluble in an aqueous (hydrophilic) solution. That is, inhibitory compounds of the present invention do not need to be lipophilic as the compounds need not cross cell membranes if "delivered" by endocytosis. Furthermore, inhibitors of cellular dibasic amino acid processing endoproteases are less likely to cause severe side effects since reductions in cellular dibasic amino acid processing endoprotease activity apparently are not significantly harmful to the cell, as demonstrated, for yeast Kex2 endoprotease-deficient strains (see, for example, Julius et al., 1984, *Cell,* ibid.) and Chinese hamster ovary cell mutants that apparently lack a functional dibasic amino acid processing endoprotease as they are unable to cleave the precursor envelope proteins of Sindbis virus or Newcastle disease virus (see, for example, Moehring et al., pp. 2590–2594, 1993, *J. Biol. Chem.,* vol. 268; Inocencio et al., pp. 593–595, 1993, *J. Virology,* vol. 67).

Preferred cellular dibasic amino acid processing endoproteases include animal and plant dibasic amino acid processing endoproteases, with mammalian, avian, fish, and insect cellular dibasic amino acid processing endoproteases being more preferred, the dibasic amino acid processing endoproteases of humans, livestock and pets being even more preferred, and human, simian, feline, canine, bovine and rodent cellular dibasic amino acid processing endoproteases being even more preferred. Particularly preferred dibasic amino acid processing endoproteases to target are human dibasic amino acid processing endoproteases.

Preferred dibasic amino acid processing endoproteases include endoproteases that naturally are found in (i.e., the cellular source of which is) cell types that are capable of producing infectious viruses upon infection by an enveloped virus or cell types that produce hormones. Examples of such cell types include, but are not limited to, CD4+ T-lymphocytes (natural source of the dibasic amino acid processing endoprotease that cleaves HIV gp160; also the natural source of several lymphokines), macrophages, liver cells (natural source of furin and of the dibasic amino acid processing endoprotease that cleaves precursor hepatitis envelope; the liver is also the source of a number of prohormones that are processed by dibasic amino acid processing endoproteases), pancreatic cells (source of insulin), kidney cells (source of renin), dendritic cells, pituitary cells (source of PC1/PC3 and PC2) and neurons as well as other immune and/or brain cells. More preferred dibasic amino acid processing endoproteases include CD4+ T-lymphocyte dibasic amino acid processing endoproteases, furin, PC1 (same as PC3), PC2, PACE4, and PACE 4.1.

Dibasic amino acid processing endoproteases that are able to effect cleavage of at least one precursor envelope protein of an enveloped virus are particularly preferred, with dibasic amino acid processing endoproteases being able to cleave an HIV gp160 being more preferred. Dibasic amino acid processing endoproteases that are naturally found in cell types that are capable of producing infectious virus upon infection by a lentivirus are particularly preferred, and particularly CD4+ T-lymphocyte dibasic amino acid processing endoproteases capable of cleaving an HIV gp160 or HTLV gp69 precursor protein.

The phrase dibasic amino acid processing site refers to a site on the precursor protein that can be cleaved by a dibasic amino acid processing endoprotease. Dibasic amino acid processing sites usually include at least one pair of basic amino acid residues that are substantially adjacent to each other. Suitable sites include, but are not limited to, Lys-Arg, Arg-Arg, Lys-Lys, Pro-Arg, Lys-/Arg-X-Lys/Arg, Lys/Arg-X-X-Lys/Arg, (i.e., Lys-Xaa-Xaa-Lys (SEQ ID NO: 1), Lys-Xaa-Xaa-Arg (SEQ ID NO: 2), Arg-Xaa-Xaa-Lys (SEQ ID NO: 3), and Arg-Xaa-Xaa-Arg (SEQ ID NO: 4) ) where "Lys" is lysine, "Arg" is arginine, "Pro" is proline and "X" is any amino acid. A particularly preferred dibasic amino acid processing site is the Arg-Glu-Lys-Arg (SEQ ID NO: 5) site found in HIV gp160 precursor proteins, wherein "Glu" is glutamic acid.

The term precursor protein refers to a protein that undergoes post-translational modification during maturation, a process that includes at least one step of cleavage by a dibasic amino acid processing endoprotease at a dibasic amino acid processing site within the precursor protein to form at least one cleavage protein. The terms cleavage protein, cleaved protein, cleavage product, and cleaved product each refer to a protein that has been produced by proteolytic cleavage of a precursor protein, the cleavage being required, but not necessarily sufficient, for the protein to become mature and bioactive. It should be understood that cleavage proteins of the present invention can undergo additional post-translational maturation steps prior and/or subsequent to dibasic amino acid processing endoprotease cleavage. A precursor protein of the present invention can be a polyprotein such that the precursor protein contains more than one cleavage protein which can be separated by cleavage with a dibasic amino acid processing endoprotease. Both yeast and heterologous precursor proteins can be useful in the present invention.

The term yeast precursor protein refers to a precursor protein of the same species as the yeast strain used in the identification of inhibitory compounds in accordance with the present invention. Yeast precursor proteins are preferably produced endogenously (i.e., naturally) by the yeast strain. Any yeast precursor protein having a dibasic amino acid processing site, the cleavage of which can be detected, can be monitored to determine whether the putative inhibitory compound can inhibit the ability of a dibasic amino acid processing endoprotease to cleave a heterologous precursor protein. Suitable yeast precursor proteins include, but are not limited to precursor proteins of α-factor mating pheromones and killer toxins. A preferred yeast precursor protein to monitor is a precursor α-factor protein.

The phrases a precursor protein heterologous to a yeast precursor protein and a heterologous precursor protein each refer to a precursor protein that is naturally produced in a cell type other than the yeast strain used in the identification of inhibitory compounds in accordance with the present invention. The heterologous precursor protein can be, for example, a precursor protein of an infectious agent or a labeled precursor protein that can be used as a marker in the method to identify compounds that inhibit dibasic amino acid processing endoproteases. A heterologous precursor protein can be produced by a yeast strain of the present invention by genetically engineering the yeast strain to produce the protein, using recombinant techniques known to those skilled in the art to insert the gene encoding the protein into the yeast strain in a manner such that the yeast strain is capable of expressing (i.e., producing) the precursor protein (see, for example, Sambrook et al., *Molecular Cloning: A Laboratory Manual*, Cold Spring Harbor Labs Press, 1989; Pichuantes et al., in *Principles and Practice of Protein Engineering*, Hanser, 1993, in press, Cleland and Craik, eds.).

Heterologous precursor proteins can be from any species, including viral, bacterial, fungal, plant, and animal, including human, precursor proteins, with viral, bacterial, and parasite precursor proteins being preferred, and viral precursor proteins being more preferred. Preferred precursor proteins include precursor proteins, the cleavage products (i.e., cleavage proteins) of which are important in, and often critical for, the production of an infectious agent. As such, preferred heterologous precursor proteins include precursor viral envelope proteins, such as the precursor envelope proteins of enveloped viruses such as retroviruses, herpes viruses, hepadnaviruses, pox viruses, orthomyxoviruses, paramyxoviruses, rhabdoviruses, togaviruses, arena viruses, bunyaviruses and coronaviruses, with precursor envelope proteins of retroviruses, herpes viruses and hepatitis viruses being more preferred. Particularly preferred precursor proteins are precursor envelope proteins of T-lymphotrophic viruses, such as human T-cell lymphotrophic virus (HTLV), bovine leukemia virus (BLV) and feline leukemia virus (FLV), with HTLV-I gp69, HTLV-II gp69, and functional equivalents thereof being more preferred lymphotrophic precursor proteins. Also particularly preferred are the precursor proteins of lentiviruses, such as simian (SIV), feline (FIV), canine (CIV), and human (HIV) immunodeficiency viruses, with HIV-1 gp160, HIV-2 gp160, and functional equivalents thereof, being particularly preferred lentivirus precursor proteins.

One preferred class of heterologous precursor proteins is a precursor protein that includes at least one protein segment that enhances correct processing of the precursor protein in the yeast Golgi apparatus and/or export (e.g., proper folding, other post-translational modifications and migration) through the yeast secretory pathway. Without being bound by theory, it is believed that a yeast protein segment, such as a natural "pro" or "leader" sequence of a proprotein and/or a dibasic amino acid processing site, joined to a heterologous precursor protein may improve the likelihood of efficient maturation (e.g., export and processing) of the precursor protein. It has been found that attachment of yeast leader segments, such as α-factor, invertase and carboxypeptidase Y leader segments, to otherwise mature heterologous proteins promotes proper folding and migration of the proteins through the secretory pathway (see, for example, Graham et al., pp. 209–218, 1991, *J. Cell Biology*, vol. 114). Preferred yeast segments for use in the present invention include yeast α-factor mating pheromone leader sequences, yeast α-factor dibasic amino acid processing sites and yeast α-factor mating pheromone leader sequences joined to yeast α-factor dibasic amino acid processing sites. A particularly preferred precursor protein of the present invention is an α-factor mating pheromone leader and α-factor dibasic amino acid processing site joined to an HIV precursor protein.

The use of a yeast-based assay in the present invention, particularly as an initial screen, to identify compounds that inhibit heterologous dibasic amino acid processing endoproteases (i.e., dibasic amino acid processing endoproteases of organisms other than the yeast species used in the assay) has several advantages. As a eukaryote, yeast have subcellular organelles and are able to perform many post-translational modifications in a manner similar to that effected by mammalian cells, such as N-terminal myristylation, prenylation, acetylation, phosphorylation, removal of N-terminal methionine, N- and O-linked glycosylation, disulfide bridge formation and protein oligomerization. Like bacteria, yeast are easy to manipulate both genetically and biochemically, easy to transform, grow rapidly (doubling times of about 1.5 to about 4 hours) on inexpensive medium, and produce heterologous proteins in large quantities. Thus, a yeast-based assay is less complicated, less expensive, and less time-consuming than an animal cell or plant cell-based assay for the identification of animal or plant dibasic amino acid processing endoproteases. A number of putative inhibitory compounds can be screened in a rapid manner, either as pools of compounds or individually. Furthermore, a yeast-based assay to identify inhibitors of dibasic amino acid processing endoproteases that otherwise would enable propagation and spread of infectious agents obviates the need to work with live infectious agents to identify such inhibitory compounds. In addition, yeast can be genetically and recombinantly manipulated in a straightforward manner to obtain strains that produce heterologous precursor proteins and/or heterologous dibasic amino acid processing endoproteases. Use of yeast strains that lack a functional yeast Kex2 endoprotease but that can express a particular heterologous dibasic amino acid processing endoprotease for which inhibitors are desired, reduces potential interference by other cellular components being expressed by the cell type that endogenously (i.e., naturally) produces the particular dibasic amino acid processing endoprotease. Although yeast have been used to produce a variety of heterologous proteins including subunit viral vaccines (for review, see, for example, Pichuantes et al., 1993, ibid.), the inventor is unaware of the use of yeast strains to identify a compound capable of inhibiting a dibasic amino acid processing endoprotease, and particularly to identify a compound that, because it is able to inhibit a dibasic amino acid processing endoprotease, can be used to treat infections.

Suitable yeast strains to use in the present invention include any yeast strain that has a dibasic amino acid processing endoprotease capable of cleaving a dibasic amino acid processing site on a precursor protein or any yeast strain that can be transformed to produce such an endoprotease. The yeast can be haploid, diploid, or polyploid. Yeasts with higher ploidy typically exhibit less deleterious mutation effects. Preferred yeast strains include strains of the genera Saccharomyces, Pichia, Hansenula, Schizosaccharomyces, Kluyveromyces, Yarrowia and Candida. Preferred species include *Saccharomyces cerevisiae, Pichia pastoris, Hansenula polymorpha, Schizosaccharomyces pombe, Kluyveromyces lactis, Yarrowia lipolytica* and *Candida maltosa. Saccharomyces cerevisiae* strains are particularly preferred because of the versatility of such strains including the ease with which such strains can be manipulated genetically and recombinantly, the ease with such strains can be cultured and induced to produce heterologous proteins, and the variety of strain available for use.

For certain embodiments, Kex2 endoprotease-deficient yeast strains are preferred. Such strains can be produced using a variety of methods known to those skilled in the art, preferably by genetic modification. A preferred genetic method to produce a Kex2 endoprotease-deficient strain is gene replacement (see, for example, Fuller et al., pp. 482–486, 1989, Science, vol. 246; and Franzusoff et al., pp. 27–37, 1991, J. Cell. Biol., vol. 112).

Transformation of a heterologous gene (e.g., a heterologous dibasic amino acid processing endoprotease gene or a heterologous precursor protein gene) into a yeast strain can be accomplished by any method by which a gene is inserted into a cell. Transformation techniques include, but are not limited to, transfection, electroporation, lipofection, bacterial transfer and spheroplast fusion. Genes transformed into yeast cells can either remain on extrachromosomal vectors or be integrated into the host genome. The term gene includes any nucleic acid sequence encoding the desired protein. The desired protein can be the natural full-length protein, or can be a functionally equivalent protein in which amino acids have been deleted (e.g., a truncated version of the protein), inserted, inverted, substituted and/or derivatized (e.g., acetylated, glycosylated, phosphorylated, tethered by a glycophosphatidyl inositol (GPI) anchor) such that the modified protein has a biological function substantially similar to that of the natural protein. Modifications can be accomplished by techniques known in the art including, but not limited to, direct modifications to the protein or modifications to the gene encoding the protein using, for example, classic or recombinant DNA techniques to effect random or targeted mutagenesis. Functionally equivalent proteins can be selected using assays set up to measure the biological activity of the protein. The term functionally equivalent protein refers to a protein having a similar biological activity as the natural protein. As such, a functionally equivalent precursor protein would have a similar biological activity as the corresponding natural precursor protein. A functionally equivalent dibasic amino acid processing endoprotease would have a similar ability to cleave a precursor protein having a dibasic amino acid processing site as the corresponding natural endoprotease.

Expression of a heterologous dibasic amino acid processing endoprotease or precursor protein in a yeast strain is accomplished using techniques known to those skilled in the art. Briefly, the gene encoding the dibasic amino acid processing endoprotease or precursor protein is inserted into an expression vector in such a manner that the gene is operatively joined to a transcription control sequence in order to be capable of effecting either constitutive or regulated expression of the gene when the gene is transformed into a host yeast cell. Dibasic amino acid processing endoprotease and/or precursor protein genes can be on one or more expression vectors operatively linked to one or more transcription control sequences. A recombinant molecule herein refers to a gene operatively linked to at least one transcription control sequence on an expression vector. An expression vector herein refers to a DNA or RNA vector that is capable of transforming a host cell, of replicating within the host cell, and of effecting expression of the operatively linked gene. Expression vectors can be capable of replicating to either a high or low copy number depending on their inherent characteristics. Transcription control sequences, which can control the amount of protein produced, include sequences which control the initiation, elongation, and termination of transcription. Particularly important transcription control sequences are those which control transcription initiation, such as promoter and upstream activation sequences. Any suitable yeast promoter can be used in the present invention and a variety of such promoters are known to those skilled in the art. Preferred promoters for expression in *Saccharomyces cerevisiae* include, but are not limited to, promoters of genes encoding the following yeast proteins: alcohol dehydrogenase I (ADH1) or II (ADH2), phosphoglycerate kinase (PGK), triose phosphate isomerase (TPI), glyceraldehyde-3-phosphate dehydrogenase (GAPDH), galactokinase (GAL1), galactose-1-phosphate uridyltransferase (GAL7), UDP-galactose epimerase (GAL10), cytochrome $c_1$ (CYC1) and acid phosphatase (PHO5), with hybrid promoters such as ADH2/GAPDH and CYC1/GAL10 promoters being more preferred, and the ADH2/GAPDH promoter, which is induced when glucose concentrations in the cell are low (e.g., about 0.1 to about 0.2 percent), being even more preferred. Likewise, a number of upstream activation sequences (UASs), also referred to as enhancers, are known. Preferred upstream activation sequences for expression in *Saccharomyces cerevisiae* include, but are not limited to, the UASs of genes encoding the following proteins: CYC1, ADH2, GAL1, GAL7 and GAL10, as well as other UASs activated by the GAL4 gene product, with the ADH2 UAS being particularly preferred. Since the ADH2 UAS is activated by the ADR1 gene product, it is preferable to overexpress the ADR1 gene when a heterologous gene is operatively linked to the ADH2 UAS. Preferred transcription termination sequences for expression in *Saccharomyces cerevisiae* include the termination sequences of the α-factor, GAPDH, and CYC1 genes.

Preferred transcription control sequences to express genes in methyltrophic yeast include the transcription control regions of the genes encoding alcohol oxidase and formate dehydrogenase.

The conditions under which the yeast strain is contacted with (e.g., mixed with, exposed to) the putative inhibitory compound are conditions in which the yeast strain can normally cleave a precursor protein having a dibasic amino acid processing site if essentially no inhibitor is present. Such conditions include an effective medium in which the yeast strain can be cultured such that the Kex2 endoprotease, a functional equivalent thereof, or a heterologous dibasic amino acid processing endoprotease produced by the yeast can exhibit biological activity (i.e., is capable of cleaving precursor proteins). An effective medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium. Yeast strains of the present invention can be cultured in a variety of containers, including, but not limited to, bioreactors, test tubes, microtiter dishes, and petri plates. Culturing is carried out at a temperature, pH and oxygen content appropriate for the yeast strain. Such culturing conditions are well within the expertise of one of ordinary skill in the art (see, for example, Guthrie et al. (eds.), 1991, *Methods in Enzymology*, vol. 194, Academic Press, San Diego). Examples of preferred conditions are included in the Examples section.

The present invention includes any of a variety of methods to determine if putative inhibitory compounds contacted with the yeast strain can inhibit cleavage of a yeast or heterologous precursor protein, including in vivo plate assays, such as the α-factor zone clearing, or halo, assay (described below) and killer toxin halo assay; methods to separate precursor and cleavage proteins, such as chromatography, electrophoresis, filtration and chemical modification (e.g., biotinylation to detect presence of cleavage protein on cell surface); methods to directly measure cleavage (e.g., use of fluorigenic peptides which emit fluorescent light when cleaved); and antibody-based methods to detect and discriminate between precursor and cleavage proteins, such as immunoprecipitation followed by gel electrophoresis and immunoblot assays. Another method to detect cleavage is to culture yeast spheroplasts, in which case cleaved proteins are secreted into the medium, which can be analyzed by enzyme immunoassay (e.g., ELISA) or radioimmunoassay. Antibodies that selectively bind to a given precursor protein or its cleaved product can be produced using standard techniques, or purchased when available. Antibodies against an infectious agent can be isolated from the infected animal's serum. Examples of the use of such methods is provided in the Examples.

In one embodiment, secretion of cleaved proteins into the culture medium is detected using a dipstick assay in which, for example, an antibody raised against the cleaved protein is attached to the dipstick. If cleavage of the precursor protein is critical for syncytium formation (e.g., a precursor retroviral envelope protein), putative inhibitory compounds may be tested for their ability to prevent syncytium formation of envelope protein-expressing yeast spheroplasts with cells expressing receptors for the retrovirus.

The α-factor zone clearing assay is a preferred method for determining the ability of a putative inhibitory compound to inhibit a dibasic amino acid processing endoprotease by comparing the extent to which a precursor yeast α-factor protein is cleaved into α-factor mating pheromones in the presence and absence of the compound. Briefly, the α-factor zone clearing assay is an agar diffusion assay based on the property that α-factor mating pheromones secreted by a yeast strain of one mating type inhibit the growth of a yeast strain of the opposite mating type in order to synchronize the cell cycles of the two mating types (see, for example, Julius et al., pp. 839–852, 1983, *Cell*, vol. 32, 839–852; Julius et al., 1984, *Cell*, ibid.). In the α-factor zone clearing assay, yeast of one mating type (e.g., mating type a, or MATa) are spread onto a culture medium-containing agar gel to form a lawn. Preferred strains with which to form a lawn include *Saccharomyces cerevisiae* MATa sst1 and MATa sst2 strains which, respectively, are about 10–30 and about 100–300 times as sensitive to α-factors than are wild-type MATa strains; and strains that do not secrete proteases, such as *Saccharomyces cerevisiae* MATa bar1 strains. The lawn can then be overlaid with yeast of the opposite mating type (e.g., mating type α, or Matα), usually such that a patch of yeast colonies can form. Alternatively, Matα yeast strains can be cultured in a reaction container, such as a test tube or microtiter dish well, and aliquots of the culture medium (containing α-factor produced by the strain) spotted onto the lawn. If the Matα yeast are capable of producing mature α-factor mating pheromones, the colonies or culture medium therefrom will inhibit the growth of the lawn, leading to the formation of a clearing zone, or halo, around the yeast colonies or spotted medium. The radius of the halo of growth inhibition (i.e., the clearing zone) is logarithmically proportional to the amount of α-factor produced by the yeast colonies, and, as such is proportional to the amount of cleavage effected by Kex2 endoprotease. Yeast strains lacking a functional Kex2 protein can grow but do not produce a clearing zone since such strains are unable to cleave precursor α-factor proteins to produce mature α-factor mating pheromones.

According to one embodiment of the present invention, the α-factor zone clearing assay can be used to determine whether putative inhibitory compounds can inhibit dibasic amino acid processing endoproteases. The assay includes overlaying yeast strains that are normally capable of producing mature α-factor mating pheromones onto lawns of yeast of the opposite mating type grown on solid culture medium. If no inhibitory compounds are added to the culture medium, the colonies will produce clearing zones. If a compound that inhibits the Kex2 endoprotease is added to the culture medium, the clearing zone of the colony exhibiting inhibition will decrease compared to a colony that is not inhibited, the amount of decrease being directly proportional to the decrease in amount of secreted α-factor and, thus, to the amount of Kex2 activity in the presence of the inhibitor. As such, when putative inhibitory compounds are added to the culture medium, the size of the resulting clearing zone is a quantitative measure of the extent of inhibition of Kex2 endoprotease by the compound. Thus, the α-factor zone clearing assay allows one to determine the efficacy of the putative inhibitory compound to inhibit a dibasic amino acid processing endoprotease from cleaving a precursor protein of the present invention. Comparison of the growth rates of yeast in the presence and absence of the putative inhibitory compound can be indicative of the cytotoxicity of the compound. Preferred compounds show little or essentially no cytotoxic side effects when administered in effective doses.

The α-factor zone clearing assay can also be used to determine the ability of a compound to inhibit a heterologous dibasic amino acid processing endoprotease expressed by a yeast strain since, in accordance with the present invention, it is believed that a heterologous dibasic amino acid processing endoprotease can cleave a precursor α-factor protein. In such an assay, a Kex2 endoprotease-deficient yeast strain that expresses a heterologous dibasic amino acid processing endoprotease (e.g., the human CD4+ T-lymphocyte dibasic amino acid processing endoprotease) is overlaid onto a lawn of yeast of the opposite mating type such that the yeast strain forms colonies. Putative inhibitory compounds are added to the culture medium and the resultant clearing zone determined and correlated with the ability of the compound to inhibit cleavage, as heretofore described.

The α-factor zone clearing assay can also be used to screen a number of putative inhibitory compounds or dosages simultaneously by culturing the yeast to be assayed (which can either be expressing its own Kex2 endoprotease or have been genetically engineered to express a heterologous dibasic amino acid processing endoprotease instead) in microtiter dish wells in the presence or absence of varying amounts of putative inhibitory compounds. Since mature α-factor mating pheromones are secreted into the culture medium, endoprotease activity can be monitored by removing aliquots of culture medium from the microtiter dish wells and applying such aliquots to a lawn of yeast of the opposite mating type. The lawn is subsequently cultured and clearing zone analyzed as heretofore described.

The present invention includes inhibitory compounds identified by the assay methods of the present invention. The term inhibitory compound refers to a compound that inhibits a dibasic amino acid processing endoprotease. A putative inhibitory compound is a compound that is being tested to determine if it is capable of inhibiting the dibasic amino acid processing endoprotease. The ability of a compound to inhibit a dibasic amino acid processing endoprotease refers to the ability of the compound to reduce the activity of the endoprotease, preferably to the extent that a substantial amount of precursor protein is not cleaved compared to cleavage effected by the endoprotease in the absence of the compound. The inhibition is preferably sufficient to interfere with the ability of an infectious agent that requires cleavage of such a precursor protein to propagate and spread to other cell types; that is, the inhibitor is able to reduce disease progression by the infectious agent. Inhibition of retroviral infection preferably includes reduction in infectivity, syncytium formation, and fusion between infected and uninfected cells.

A preferred inhibitory compound of the present invention is one that is specific for the dibasic amino acid processing endoprotease being targeted but that does not substantially adversely affect other cellular components, including other classes of proteases. That is, the compound can inhibit the targeted dibasic amino acid processing endoprotease with fewer side effects than drugs currently used for treatment, such as nucleoside analogs. Preferred inhibitory compounds are peptides, mimetopes, or mixtures thereof. As used herein, a mimetope is any organic compound that mimics the ability of a peptide to inhibit cleavage by a dibasic amino acid processing endoprotease. Mimetopes can be peptides in which the scissile peptide bond is replaced by a bond that cannot be cleaved by the endoprotease, for example by introducing a thio group. Alternatively, mimetopes can be synthetic or natural organic molecules, including nucleic acids, that have a structure similar to the dibasic amino acid processing site and, as such, bind with high affinity to the dibasic amino acid processing endoprotease.

A preferred concentration of the inhibitory compound to use in treatment is less than about 100 micromolar ($\mu$M), more preferably in the range of about 1 to about 10 $\mu$M and even more preferably in the range of about 1 to about 300 nanomolar (nM), which is the concentration at which apparently useful inhibitors of the HIV-1 encoded aspartyl protease are being administered. Inhibitory compounds delivered in such concentration ranges preferably inhibit at least about 50, and more preferably at least about 65, and even more preferably at least about 75 percent of the activity of the targeted dibasic amino acid processing endoprotease.

The inhibitory compound can effect either permanent or temporary inhibition by, for example, binding, respectively, irreversibly or reversibly to the dibasic amino acid processing endoprotease. The inhibitory compound may also modify the dibasic amino acid processing endoprotease, for example, by chemically inactivating the dibasic amino acid processing endoprotease. For example, an alkylating agent, such as chlorambucil, can be attached to a peptide having a dibasic amino acid processing site or a mimetope of such a peptide.

The inhibitory compound can further include a component that permits targeting of the compound to a particular cell type capable of producing the dibasic amino acid processing endoprotease. Such a component can include any substance that binds selectively to the cell type, such as an antibody, hormone, lymphokine, other ligand, or even a part of a viral envelope protein capable of binding to a receptor on the targeted cell type (e.g., at least a portion of HIV gp120 that can target the CD4 receptor on human CD4+ T-lymphocytes.), or portions thereof that retain binding activity.

Particularly preferred inhibitory compounds of the present invention are capable of (a) inhibiting α-factor processing by yeast strains of the present invention as shown by the α-factor zone clearing assay; (b) inhibiting in vitro processing of yeast α-factor by a secreted soluble yeast Kex2 endoprotease, such as that described by Fuller et al., pp. 482-486, 1989, Science, vol. 246; (c) inhibiting in vitro processing of the precursor protein that is normally cleaved by the targeted dibasic amino acid processing endoprotease in an assay using a secreted soluble form of the targeted dibasic amino acid processing endoprotease; and (d) inhibiting processing by yeast of the precursor protein normally cleaved by the targeted dibasic amino acid processing endoprotease, the processing otherwise being effected by Kex2 or by the heterologous dibasic amino acid processing endoprotease. Preferred inhibitory compounds of the present invention are antiviral compounds and, as such, are also able to inhibit syncytium formation and formation of infectious virions. Particularly preferred antiviral compounds are capable of preventing the spread of HIV, and, as such, are capable of inhibiting syncytium formation "in vivo" in gp160-containing cells (e.g., HIV-infected CD4+ T-lymphocytes or HIV-infected CD4-containing HeLa cells) and of inhibiting the formation of infectious HIV virions.

One aspect of the present invention is the selection of putative inhibitory compounds to test in accordance with the present invention. Any compound can be tested; however, a preferred method to select putative inhibitory compounds is to follow a strategy similar to that used in identifying other protease inhibitors, such as inhibitors of the HIV-1 encoded aspartyl protease. For example, peptides and mimetopes having a site that apparently can bind to the targeted dibasic amino acid processing endoprotease (e.g., a dibasic amino acid processing site) can be tested to identify those compounds which bind to the dibasic amino acid processing endoprotease and inhibit cleavage. Peptides and mimetopes to be tested can be compounds that have the potential for inhibiting the targeted dibasic amino acid processing endoprotease in one or more ways known to those skilled in the art, including, but not limited to, competitive inhibition, substantially irreversible binding, and modification of the dibasic amino acid processing endoprotease by the inhibitory compound (e.g., by alkylation). Peptides and mimetopes to be tested can include end groups to reduce degradation and/or labels, such as colorimetric or fluorescent tags, that are "activated" or "deactivated" upon cleavage by a dibasic amino acid processing endoprotease. One example is a fluorigenic peptide, such as Boc-Gln-Arg-Arg-MCA (tert-butoxycarbonyl-glutamine-arginine-arginine-methylcoumarin amide) in which the tag is methyl coumarin, a compound that emits fluorescence upon light activation when cleaved from the peptide. Putative inhibitory compounds can be tested in pools, using techniques known to those skilled in the art. Putative inhibitory compounds can be produced using techniques known to those skilled in the art.

One embodiment of the present invention is the identification of inhibitory compounds that reduce the infectivity of an infectious agent; that is the compounds are capable of reducing, or inhibiting, the propagation or spread of an infectious agent through a host, thereby decreasing or preventing further infection and/or disease otherwise caused by the infectious agent. Infectious agents are capable of spreading through host organisms by infecting cells, replicating and infecting additional cells, often causing disease. Infectious agents include viruses, bacteria, fungi, other parasites, and any other agents that effect infection and disease, particularly in animals and plants, and more particularly in animals. Preferred infectious agents to target with inhibitory drug compounds are enveloped viruses, such as retroviruses (e.g., lentiviruses, such as immunodeficiency viruses; type A cisternaviruses; type B oncoviruses, such as mammary tumor viruses; type C oncoviruses, such as human lymphotrophic viruses, leukemia viruses, sarcoma viruses, leukosis viruses; type D oncoviruses; and type F spumaviruses), herpes viruses (e.g., cytomegaloviruses, herpes simplex, varicella-herpes zoster, and Epstein-Barr viruses), hepadnaviruses (e.g., hepatitis A, B, C, D, E, and other non-A, non-B hepatitis viruses), poxviruses (e.g., variola and vaccinia viruses), orthomyxoviruses (e.g., influenza viruses), paramyxoviruses (e.g., measles, mumps, para influenza, Sendai and Newcastle disease viruses), rhabdoviruses (e.g., filoviridae, rabies and vesicular stomatitis virus), togaviruses (e.g. flaviviruses and alphaviruses), arena viruses, bunyaviruses and coronaviruses. Retroviruses, herpes viruses, and hepatitis viruses are more preferred infectious agents to target, with leukemia, lymphotrophic, sarcoma and lentiviruses being even more preferred. Particularly preferred lymphotrophic viruses include HTLVs, such as HTLV-I and HTLV-II; BLVs; and FLVs. Particularly preferred lentiviruses include HIV, SIV, FIV, and CIV, with HIV-1 and HIV-2 being even more preferred.

One embodiment of the present invention is the use of a yeast strain that need not be genetically engineered to identify a compound that inhibits a dibasic amino acid processing endoprotease from cleaving a precursor protein other than a yeast precursor protein (i.e., a heterologous precursor protein) by determining the ability of the yeast Kex2 endoprotease or functional equivalent thereof to cleave a yeast precursor protein in the presence and absence of the putative inhibitory compound which can, but need not be, pre-incubated with the yeast strain prior to induction of yeast precursor protein expression. In an alternative embodiment, the yeast strain can be Kex2-endoprotease deficient and produce a heterologous dibasic amino acid processing endoprotease that is tested for its ability to cleave the yeast precursor protein in the presence and absence of the putative inhibitory compound which can, but need not be, pre-incubated with the yeast strain prior to induction of yeast precursor protein expression.

Another embodiment of the present invention is use of a yeast strain capable of producing a heterologous precursor protein to identify a compound that inhibits a dibasic amino acid processing endoprotease from cleaving a heterologous precursor protein by determining the ability of the yeast Kex2 endoprotease or functional equivalent thereof to cleave the heterologous precursor protein in the presence and absence of the putative inhibitory compound, which can, but need not be, pre-incubated with the yeast strain prior to induction of heterologous precursor protein expression. A yeast strain capable of producing a heterologous precursor protein is a yeast strain that is transformed with a gene encoding the precursor protein in such a manner that the precursor protein can be expressed by the yeast, using heretofore described transformation and expression methods. Alteratively, the yeast strain can be Kex2-endoprotease deficient and produce a heterologous dibasic amino acid processing endoprotease that is tested for its ability to cleave the heterologous precursor protein in the presence and absence of the putative inhibitory compound which can, but need not be, preincubated with the yeast strain prior to induction of heterologous precursor protein expression. A preferred yeast strain to use in this embodiment is a *Saccharomyces cerevisiae* yeast strain that produces a precursor viral envelope protein and more preferably an HIV gp160 protein, such as HIV-1 gp160, HIV-2 gp160, or a functional equivalent thereof. Preferred Kex2 endoprotease-deficient yeast strains are *Saccharomyces cerevisiae* strains that produce both a precursor viral envelope protein and a dibasic amino acid processing endoprotease that is capable of cleaving the precursor viral envelope protein. A particularly preferred yeast strain to use is a Kex2 endoprotease-deficient *Saccharomyces cerevisiae* strain that produces an HIV gp160 protein, such as HIV-1 gp160, HIV-2 gp160, or a functional equivalent thereof and a human CD4+ T-lymphocyte dibasic amino acid processing endoprotease responsible for cleaving the HIV gp160 protein.

Another embodiment of the present invention is a method to identify a compound that inhibits an animal or plant dibasic amino acid processing endoprotease in vitro that includes contacting a putative inhibitory compound with a secreted soluble dibasic amino acid processing endoprotease, such as a yeast Kex2 protein fragment or an animal or plant dibasic amino acid processing endoprotease fragment, and determining if the putative inhibitory compound is capable of inhibiting cleavage by the secreted soluble dibasic amino acid processing endoprotease. As used herein, a secreted soluble dibasic amino acid processing endoprotease is a dibasic amino acid processing endoprotease fragment that retains proteolytic activity but that essentially lacks the transmembrane and C-terminal cytosolic domains. As such, the enzyme can be secreted into the culture medium. Such dibasic amino acid processing endoprotease fragments can be produced in a manner analogous to that described for yeast ssKex2 (see, for example, Fuller et al., pp. 1434–1438, 1989, *Proc. Natl. Acad. Sci.,* vol. 86; Fuller et al., pp. 482–486, 1989, *Science,* vol. 246; Brenner et al., pp. 922–926, 1992, *Proc. Natl. Acad. Sci.,* vol. 89). A preferred dibasic amino acid processing endoprotease for use is a yeast Kex2 protein fragment, with *Saccharomyces cerevisiae* ssKex2 protein being even more preferred. Another preferred dibasic amino acid processing endoprotease to use is a human CD4+ T-lymphocyte dibasic amino acid processing endoprotease. The ability of a putative inhibitory compound to inhibit dibasic amino acid processing endoprotease cleavage can be determined in a variety of ways as heretofore described, including the α-factor zone clearing assay, methods to separate precursor and cleavage proteins, methods to directly measure cleavage, and antibody-based methods to detect and discriminate between precursor and cleavage proteins.

Another embodiment of the present invention is a method to screen for compounds that inhibit the cleavage of a heterologous precursor protein by a heterologous dibasic amino acid processing endoprotease which includes several screening stages of increasing specificity. Such a method enables one skilled in the art to rapidly select an inhibitory compound of desired specificity from a large group of putative inhibitory compounds. It should be recognized that not all of the following screening stages are required and that one or more stages can be used in a variety of combinations and orders. The stages are listed essentially in order of increasing specificity. Inhibitory compounds can be screened either in pools of compounds or individually.

According to one embodiment of the present invention, one conducts a first stage screen of a large group of putative inhibitory compounds by contacting the compounds with yeast strains that need not have been genetically engineered and determining whether cleavage of precursor yeast proteins having dibasic amino acid processing sites (e.g., α-factor mating pheromones) is occurring in the presence of increasing concentrations of the putative inhibitory compounds. Such a screen is based on the aforementioned discovery that yeast Kex2 endoproteases appear to behave similarly to other dibasic amino acid processing endoproteases and, as such, compounds that inhibit Kex2 endoprotease are likely to inhibit other dibasic amino acid processing endoproteases.

Putative inhibitory compounds that exhibit inhibition in the first stage screen can then be submitted to a second stage screen which includes contacting the compounds with yeast strains that lack a functional yeast Kex2 endoprotease but express the heterologous dibasic amino acid processing endoprotease against which inhibitory compounds are desired (i.e., the targeted dibasic amino acid processing endoprotease) and determining whether the putative inhibitory compounds are able to inhibit the heterologous dibasic amino acid processing endoprotease from cleaving a precursor yeast protein having a dibasic amino acid processing site (e.g., α-factor mating pheromones). Alternatively, prior to the second stage screen, putative inhibitory compounds that exhibit inhibition in the first stage screen can be submitted to an intermediate screen which includes contacting the compounds with yeast strains that have a functional Kex2 endoprotease and that express the heterologous precursor protein normally cleaved by the heterologous dibasic amino acid processing endoprotease and determining whether such putative inhibitory compounds are capable of inhibiting cleavage of the heterologous precursor protein. Putative inhibitory compounds that are found to inhibit cleavage of the heterologous precursor protein (i.e., candidate inhibitory compounds) can then be submitted to the second or third stage screen.

Candidate inhibitory compounds that exhibit inhibition in the intermediate and/or second stage screen can then be submitted to a third stage screen to measure inhibitory activity in yeast strains that lack a functional yeast Kex2 endoprotease but express both the heterologous dibasic amino acid processing endoprotease against which inhibitory compounds are desired and the heterologous precursor protein normally cleaved by the heterologous dibasic amino acid processing endoprotease. An advantage of such a screen is to identify compounds that inhibit cleavage of the heterologous precursor protein by the heterologous dibasic amino acid processing endoprotease with high specificity and affinity. It is known that dibasic amino acid processing endoproteases cleave different precursor proteins with different affinities (see, for example, Barr, 1991, *Cell,* ibid.; Bresnahan et al., pp. 2851–2859, 1990, *J. Cell Biol.,* vol. 111; Hosaka et al., pp. 12127–12130, 1991, *J. Biol. Chem.,* vol. 266; Oda et al., pp. 1181–1186, 1991, *Biochem. Biophys. Res. Comm.,* vol 179; Thim et al., pp. 6766–6770, 1986, *Proc. Natl. Acad. Sci. USA,* vol. 83). In order to obtain an inhibitor that is particularly specific against a targeted dibasic amino acid processing endoprotease, it is desirable to test candidate inhibitory compounds against the dibasic amino acid processing endoprotease and precursor protein to which the desired inhibitor is targeted in vivo.

An additional stage in which the candidate inhibitory compound is subjected to an in vitro assay in which the ability of the compound to inhibit cleavage by either yeast ssKex2 or by a secreted soluble heterologous dibasic amino acid processing endoprotease corresponding to the protease that naturally cleaves the heterologous precursor protein can also be conducted before or after any of the aforementioned stages.

The ability of candidate inhibitory compounds that exhibit inhibition in the third stage screen to actually inhibit the targeted dibasic amino acid processing endoprotease in the cell type in which the targeted dibasic amino acid processing endoprotease is endogenously produced can then be verified by contacting such compounds with such a cell type and determining the extent of inhibition of precursor protein cleavage by the targeted dibasic amino acid processing endoprotease at various concentrations of the inhibitory compounds. For example, candidate inhibitors of HIV infection can be contacted with infected human CD4+ T-lymphocytes to determine if the inhibitors can reduce or block syncytium formation, membrane fusion, and production of infectious virus using standard assays (see, for example, McCune et al., 1988, *Cell*, ibid.; Kowalski et al., 1987, *Science*, ibid.; Sodroski et al., 1986, *Nature*, ibid.). This final stage allows the identification of the most selective dibasic amino acid processing endoprotease inhibitory compounds, verifies appropriate dosage ranges for the inhibitory compounds, and enables the determination of the amount of conversion of gp160 to gp120 that is tolerable while maintaining an antiviral effect.

The present invention also includes yeast strains capable of producing a heterologous precursor protein having a dibasic amino acid processing site that are also capable of cleaving the precursor protein into at least one cleavage protein. Preferred yeast strains are capable of processing a precursor protein to the extent required to produce a mature, bioactive protein. In one embodiment the yeast strains are Kex2 endoprotease-deficient yeast strains that produce a heterologous dibasic amino acid processing endoprotease. Although a variety of yeast strains are included in the present invention, as heretofore disclosed, preferred yeast strains are of the species *Saccharomyces cerevisiae*. Particularly preferred *Saccharomyces cerevisiae* strains produce HIV gp160 precursor proteins. Additional particularly preferred strains are Kex2 endoprotease-deficient *Saccharomyces cerevisiae* strains that produce dibasic amino acid processing endoproteases that cleave gp160 and Kex2 endoprotease-deficient *Saccharomyces cerevisiae* strains that produce both HIV gp160 precursor proteins and dibasic amino acid processing endoproteases that cleave gp160.

Additional preferred yeast strains of the present invention include Kex2 endoprotease-deficient strains, including Kex2 endoprotease deficient strains that produce a heterologous precursor protein. Preferred Kex2 endoprotease-deficient yeast strains are also deficient in at least one (i.e., lacks at least one functional) soluble vacuolar protease, such as proteinase A (encoded in *Saccharomyces cerevisiae* by PRA, or PEP4), proteinase B (encoded in *Saccharomyces cerevisiae* by PRB), and/or proteinase C (encoded in *Saccharomyces cerevisiae* by PRC, or CPY). *Saccharomyces cerevisiae* strains that are deficient in proteinase A, proteinase B, and proteinase C as well as in Kex2 endoprotease are more preferred. A particularly preferred Kex2 endoprotease-deficient yeast strain is *Saccharomyces cerevisiae* kex2Δ, a Kex2 endoprotease-deficient, proteinase A-deficient, and proteinase B-deficient strain having the genotype pep4-::URA3 kex2::TRP1 prb leu2 his4 ura3 trp1 (production of *Saccharomyces cerevisiae* kex2Δ is disclosed in the Examples section). Also particularly preferred are *Saccharomyces cerevisiae* kex2Δ progeny and mutants that are Kex2 endoprotease-deficient. The phrase a yeast strain having all of the identifying characteristics of *Saccharomyces cerevisiae* kex2Δ refers to a *Saccharomyces cerevisiae* yeast strain essentially lacking Kex2, protease A and protease B proteolytic activities. Kex2 endoprotease-deficient strains are useful in the identification of a gene that encodes a dibasic amino acid processing endoprotease, such as an animal or plant dibasic amino acid processing endoprotease. When transformed with a gene encoding a heterologous dibasic amino acid processing endoprotease, Kex2 endoprotease-deficient strains are useful in the identification of compounds that inhibit the proteolytic activity of the heterologous dibasic amino acid processing endoprotease.

The present invention also includes test kits to identify a compound capable of inhibiting a dibasic amino acid processing endoprotease. Such kits include a yeast strain capable of producing and cleaving a yeast or heterologous precursor protein and a means for determining the extent of cleavage in the presence of a putative inhibitory compound. In one embodiment, the yeast strain is a Kex2 endoprotease-deficient yeast strain capable of producing a heterologous dibasic amino acid processing endoprotease. Any suitable means to determine cleavage, including those heretofore disclosed, can be used. A preferred means is the α-factor zone clearing assay, in which the extent of cleavage is indicated by the radius of the clearing zone produced in the assay. Preferred yeast strains to use in conjunction with the α-factor zone clearing assay are yeast strains that need not be genetically engineered or Kex2 endoprotease-deficient yeast strains that express a heterologous dibasic amino acid processing endoprotease. One embodiment of the present invention is a test kit based on the α-factor zone clearing assay that includes (a) a yeast strain, preferably lyophilized, that is to be tested for its ability to produce α-factor mating pheromones in the presence or absence of an inhibitory compound and (b) a yeast strain of the opposite mating type, preferably lyophilized, that can be cultured to form the lawn for the zone clearing assay. The test kit can also include the culture medium and/or containers (for example, petri dishes, microtiter dishes, etc.) in which to conduct the assay.

Another embodiment of the present invention is a test kit in which the ability of dibasic amino acid processing endoprotease to cleave a precursor protein expressed by a yeast strain is determined by detecting the cleaved product using, for example, an antibody-based assay, such as immunoprecipitation with gel electrophoresis or immunoblot analysis. Such a test kit can include (a) a yeast strain, preferably lyophilized, that is to be tested for its ability to cleave, in the presence or absence of an inhibitory compound, a heterologous precursor protein produced by the yeast strain; and (b) at least one primary antibody that selectively binds to the cleaved product. The yeast strain can be a Kex2 endoprotease-deficient strain that expresses a heterologous dibasic amino acid processing endoprotease. Alternatively, the kit can monitor the ability of the endogenous yeast Kex2 endoprotease to cleave the heterologous precursor protein. The test kit can further include a "development component" to detect binding of the primary antibody to the cleaved product (i.e., the cleavage protein). The development component can include a compound that binds to the primary antibody, the compound being coupled to a detectable tag. A binding compound can include, but is not limited to, a secondary antibody that is capable of binding to the primary antibody when the primary antibody is bound to the cleaved product; a bacterial surface protein that binds to antibodies, such as Protein A or Protein G; a biotin-streptavidin or biotin-avidin coupled detection system; a cell that interacts with antibodies, such as a T cell, B cell, or macrophage; a eukaryotic cell surface protein that binds to antibodies, such as an Fc receptor; and a complement protein. Preferred compounds include secondary antibodies, Protein A and Protein G. A variety of detectable tags can be used, including, but not limited to radioactive, enzymatic, and fluorescent labels. Detection of the tag can be accomplished using a variety of wellknown techniques, depending on the assay. For example, an enzymatic assay, (e.g., use of alkaline phosphatase or horse radish peroxidase) often yields a colorimetric product that can be detected visually or by a machine such as a densitometer or a spectrophotometer. The test kit can further include reagents for conducting immunoprecipitation and immunoblot analysis.

Another embodiment of the present invention is a test kit in which the yeast strain that is to be tested for its ability to cleave, in the presence or absence of an inhibitory compound, a heterologous precursor protein produced by the yeast strain is converted into a spheroplast. As a spheroplast, the yeast strain can secrete into the culture medium at least a portion of any cleaved product that otherwise would be localized on the cell surface. Thus, the test kit can include a detection system based on the ability to detect cleaved product in the culture medium. For example, the kit can contain a primary antibody that selectively binds to cleaved product, which can be used in, for example, an enzyme immunoassay or immunoprecipitation assay of the culture medium. Alternatively, the kit can include a solid surface, such as a dipstick, impregnated with primary antibody that selectively binds to the cleaved product. The kit can further contain a development component, as heretofore described. The yeast strain provided in the kit can be a Kex2 endoprotease-deficient strain that expresses a heterologous dibasic amino acid processing endoprotease. Alternatively, the kit can monitor the ability of the endogenous yeast Kex2 endoprotease to cleave the heterologous precursor protein.

In a preferred embodiment, test kits of the present invention are used to identify compounds that can inhibit infectious agents and thus treat or prevent disease. A particularly preferred test kit is capable of identifying compounds that reduce the infectivity of HIV. Compounds that are identified by test kits of the present invention as being able to inhibit cleavage of HIV gp160 into gp120 and gp41 can be used to treat HIV infection and to prevent or reduce the occurrence of AIDS.

The methods and test kits of the present invention are particularly useful in developing antiviral drugs that block cleavage of precursor envelope proteins by cellular dibasic amino acid processing endoproteases. One concern of targeting cellular proteases is whether the targeted cells will still function properly if the targeted dibasic amino acid processing endoproteases are inhibited by the antiviral drugs. Without being bound by theory, it is believed that inhibition of dibasic amino acid processing endoproteases will not be substantially harmful to the cells producing the dibasic amino acid processing endoproteases since Kex2 endoprotease-deficient yeast strains and Chinese hamster ovary cells apparently lacking a functional dibasic amino acid processing endoprotease are viable, as heretofore disclosed. It is contemplated, however, that if inhibition of a cellular dibasic amino acid processing endoprotease reduces maturation of a key protein normally processed by that dibasic amino acid processing endoprotease (such as a hormone), the antiviral treatment can be supplemented by such a key protein.

One aspect of the invention is the development of targeted therapies to treat HIV infection and prevent the onset of ARC or AIDS. As such, a preferred therapy is one that is targeted to the human CD4+ T-lymphocyte dibasic amino acid processing endoprotease that naturally cleaves gp160. Thus, a preferred method to prevent the spread of HIV is to (a) identify a compound that inhibits CD4+ T-lymphocyte dibasic amino acid processing endoprotease from cleaving an HIV gp160 precursor protein by (i) contacting putative inhibitory compounds with a yeast strain that produces the CD4+ T-lymphocyte dibasic amino acid processing endoprotease and (ii) selecting a compound that can reduce cleavage of gp160; and (b) administering the selected compound to a person in need of such a treatment.

The use of a test kit of the present invention in which a CD4+ T-lymphocyte dibasic amino acid processing endoprotease is produced by the yeast strain permits one to identify compounds that bind with high affinity to the correct binding pocket in the CD4+ T-lymphocyte dibasic amino acid processing endoprotease. Such compounds will be particularly useful therapeutics as they should exhibit a high specific activity that permits them to be administered in low dosages. It is also believed that relatively low doses of inhibitory compounds of the present invention will be sufficient for treatment because the relatively low abundance of yeast Kex2 endoprotease in cells and the relatively low activity of human CD4+ T-lymphocyte dibasic amino acid processing endoprotease in cleaving HIV gp160 suggest that cells produce relatively low amounts of dibasic amino acid processing endoproteases.

Targeting cellular dibasic amino acid processing endoproteases in accordance with the present invention permits inhibitory compounds to be delivered to the dibasic amino acid processing endoproteases by endocytosis, as heretofore disclosed. Inhibitory compounds of the present invention can be endocytosed by the cell membrane (fluid phase endocytosis). Alternatively, an inhibitory compound of the present invention can be a conjugate that includes a component that targets the compound to a receptor on a targeted cell type, in which case the compound is internalized by receptor mediated endocytosis.

The present invention also includes prodrugs, and production thereof, that include a dibasic amino acid processing site which are taken up by endocytosis and cleaved by dibasic amino acid processing endoproteases in the Golgi apparatus to produce an active drug. An example of a prodrug of the present invention is an active drug coupled to a positively or negative charged side group in such a manner that a dibasic amino acid processing site is situated between the active drug and the side group. The side group enables the prodrug to be hydrophilic, thereby allowing it to be soluble in bodily fluids and susceptible to endocytosis. After being endocytosed, the prodrug is transferred to the Golgi apparatus where it is cleaved by a dibasic amino acid processing endoprotease. Upon cleavage, the activated drug, if lipophilic, can migrate across the membrane into the cytoplasm of the cell. As such, the activated drug can be targeted against a cytoplasmic agent.

Another embodiment of the present invention is a method to identify a gene encoding a cellular animal or plant dibasic amino acid processing endoprotease using a Kex2 endoprotease-deficient yeast strain. A *Saccharomyces cerevisiae* Kex2 endoprotease-deficient yeast strain has been previously used to identify the *Saccharomyces cerevisiae* KEX2 gene (see, for example, Julius et al., 1984, *Cell*, ibid.). According to the present invention, a gene encoding an animal or plant dibasic amino acid processing endoprotease can be identified by a method including the steps of (a) transforming a Kex2 endoprotease-deficient yeast strain with a cDNA library prepared from RNA isolated from the desired animal or plant cell type, (b) isolating a transformed yeast strain having a functional dibasic amino acid processing endoprotease as determined by the ability of such a transformed yeast to form a clear zone in an α-factor zone-clearing assay, and (c) recovering from the transformed yeast the cDNA that includes a gene encoding the desired cellular protease. This method can preferably be used to identify genes that encode cellular proteases responsible for cleavage of precursor viral envelope proteins, such as HIV gp160 precursor proteins. As such, this method can be used to isolate the CD4+ T-lymphocyte dibasic amino acid processing endoprotease that cleaves HIV gp160 precursor proteins. The method can also include the use of a yeast strain that produces a heterologous precursor protein to identify a gene that encodes the dibasic amino acid processing endoprotease that cleaves that protein. Also included in the present invention are dibasic amino acid processing protease genes identified using this method and the proteins such genes encode.

Yet another embodiment of the present invention includes a method to improve the production in yeast strains of mature animal or plant hormones that require dibasic amino acid processing endoprotease cleavage as part of their maturation process. To date, production of such mature hormones in yeast has been relatively limited and less than efficient. Examples of such hormones for which improved production methods are needed include, but are not limited to, those disclosed in Barr et al., 1991, Cell, ibid. The method of the present invention to improve production of mature hormones in yeast includes (a) transforming a yeast strain, preferably a Kex2-deficient yeast strain, both with a gene encoding the precursor protein of the desired hormone and with a gene encoding the dibasic amino acid processing endoprotease that inherently (i.e., naturally) effects maturation of the hormone in vivo in such a manner that both genes are expressed and the resultant proteins are functional; and (b) culturing the yeast strain to produce the mature hormone. Without being bound by theory, it is believed that the dibasic amino acid processing endoprotease that naturally cleaves the hormone precursor protein can effect substantially more cleavage than can the yeast Kex2 endoprotease since the natural dibasic amino acid processing endoprotease is likely to exhibit more selectivity toward its natural processing site than is the yeast Kex2 endoprotease unless the natural processing site is the same as a yeast Kex2 processing site. Investigators have shown, for example, that the extent of cleavage is a function of the composition of the dibasic amino acid processing site and of the dibasic amino acid processing endoprotease for hormones such as insulin and renin (see, for example, Oda et al., 1991, Biochem. Biophys. Res. Comm., ibid.; Thim et al., 1986, Proc. Natl. Acad. Sci. USA, ibid.).

The present invention also includes yeast strains that effect improved production of mature hormones that require dibasic amino acid processing endoprotease cleavage as part of their maturation process. Such yeast strains, as described above, are transformed both with a gene encoding the precursor protein of the desired hormone and with a gene encoding the dibasic amino acid processing endoprotease that inherently effects maturation of the hormone in vivo in such a manner that both genes are expressed and the resultant proteins are functional.

In accordance with the present invention, a preferred embodiment of the above method is an improved method to produce insulin in yeast which includes the genetic engineering of a yeast strain to produce both the insulin precursor protein and the pancreatic dibasic amino acid processing endoprotease that naturally cleaves the insulin precursor protein in pancreatic acinar cells. As another embodiment, an improved method to produce renin in yeast includes the genetic engineering of a yeast strain to produce both the renin precursor protein and the dibasic amino acid processing endoprotease that naturally cleaves the renin precursor protein in kidney juxtaglomerular cells.

The following experimental results are provided for purposes of illustration and are not intended to limit the scope of the invention.

EXAMPLES

Example 1

This example demonstrates the in vivo ability of Saccharomyces cerevisiae to produce HIV-1 gp160 precursor envelope protein and to process gp160 into gp120 and gp41 in a manner similar to that by which mammalian cells process gp160. This example also demonstrates that Saccharomyces cerevisiae expresses at least a portion of the cleaved gp120 and gp41 proteins on its cell surface.

The envelope (env) gene encoding the gp160 precursor envelope protein (about 825 amino acids) of HIV-$1_{SF2}$ (Sanchez-Pescador et al., pp. 484–492, 1985, Science, vol. 227) (denoted HIV1 env in FIG. 1) was ligated to a nucleic acid sequence encoding an α-factor signal and leader segment of about 86 amino acids to form an α-leader/env-gene fragment (α/env) in which the signal sequence of the env gene was replaced by the α-factor signal and leader sequences in a manner similar to the method by which the epidermal growth factor gene was joined to α-factor signal and leader sequences in Brake et al., pp. 4642–4646, 1984, Proc. Natl. Acad. Sci., vol. 81. The α-factor segment (denoted α-F leader in FIG. 1) also included a dibasic amino acid processing site at its carboxyl terminus. The α/env fusion gene was operatively linked to Saccharomyces cerevisiae ADH2-/GAPDH promoter and α-factor transcription termination sequences (denoted ADH2/GAPDH promoter and α-F terminator, respectively, in FIG. 1) and joined with other yeast shuttle expression vector sequences to form recombinant molecule pα/env, depicted in FIG. 1 as pBS8. Recombinant molecule pα/env, or pBS8, contains yeast (2μ) and bacterial replication control sequences as well as a bacterial gene encoding ampicillin resistance (Amp), and auxotrophic leu2-d and prototrophic URA3 yeast genes.

Recombinant molecule pα/env was transformed into several Saccharomyces cerevisiae strains, including GPY60, a Matα pep4::URA3 prb leu2 his4 ura3 trp1 strain which is described in Baker et al., pp. 335–344, 1988, Cell, vol. 54. The transformed strain is denoted Saccharomyces cerevisiae GPY60:pα/env. Standard ligation and transformation techniques as described in Sambrook et al., ibid., and Guthrie et al. (eds.), ibid., were used in all examples.

Saccharomyces cerevisiae GPY60:pα/env was cultured in minimal medium containing 2% glucose, adenine, histidine and tryptophan at about 30° C., as described in Guthrie et al. (eds.), ibid. Expression of the α/env gene was induced by changing the carbohydrate source from glucose to raffinose. From about 2 to about 12 hours after induction, *Saccharomyces cerevisiae* GPY60:pα/env cells were lysed.

Production of α-factor segment/gp160 (α/gp160) fusion protein and its cleavage into the α-factor segment, gp120 and gp41 were monitored by immunoprecipitation followed by polyacrylamide gel electrophoresis and/or by immunoblot techniques similar to those described in Franzusoff et al., 1991, *J. Cell. Biol.*, ibid., using polyclonal α-factor antibodies (available from a number of investigators including R. Schekman, University of California, Berkeley; see also Baker et al., 1988, *Cell*, ibid.), polyclonal HIV-1$_{SF2}$ gp120 antiserum (available from the AIDS Research and Reference Reagent Program Catalog, operated by Ogden BioServices Corp., Rockville, Md.; e.g., catalog numbers 385, 387), and anti-gp160, anti-gp120, and anti-gp41 antisera isolated from the serum of HIV-1$_{SF2}$-infected individuals. Both immunoprecipitation and immunoblot studies indicated the production of α/gp160 and the ability of *Saccharomyces cerevisiae* GPY60:pα/env to effect cleavage of at least a portion of the α/gp160 into α-factor segment, gp160, α/gp120, gp120, and gp41 (note that there are Kex2 processing sites between the α-factor segment and gp160 as well as within gp160).

Production and processing of gp160 was verified by exposing *Saccharomyces cerevisiae* GPY60:pα/env cell lysates to Endoglycosidase H (available from Boehringer Mannheim Corp., Indianapolis, Ind.) under conditions similar to those described in Julius et al., 1984, *Cell*, ibid. to remove yeast glycosyl moieties from the polypeptide backbone, thereby making it easier to differentiate gp160 from gp120. Pulse chase experiments, performed in a manner similar to that described in Franzusoff et al., 1991, *J. Cell. Biol.*, ibid., also demonstrated the production of α/gp160 and its subsequent cleavage into gp120 and gp41.

A phosphorimaging calibration device (available from Molecular Dynamics, Sunnyvale, Calif.) was used to quantitate gp160 production and determine the amount of gp160 converted into gp120 and gp41 over time. It was estimated that about 5 to about 25 percent of the gp160 produced by *Saccharomyces cerevisiae* GPY60:pα/env was cleaved in vivo. This value is consistent with published reports on the efficiency (about 5 to about 15 percent) of processing in HIV-infected CD4+ T-lymphocytes in vivo (see, for example, Willey et al., pp. 9580-9584, 1988, *Proc. Natl. Acad. Sci.*, vol. 85; Earl et al., pp. 2047-2055, 1991, *J. Virology*, vol. 65).

Expression of gp120 on the cell surface of *Saccharomyces cerevisiae* GPY60:pα/env was demonstrated using the following surface protein biotinylation assay. The transformed yeast strain was cultured and gp160 expression induced as described above. About 2 to about 4 hours after induction, an aliquot of the yeast cells was exposed to the reagent NHS-LC-biotin (available from Pierce, Rockford, Ill.) using the protocol supplied by Pierce in order to biotinylate proteins present on the cell surface of the yeast strain. After quenching the excess reagent with buffers containing primary amine groups, the yeast cells were lysed, detergent-solubilized, and incubated with monomeric avidin-agarose (available from Pierce) to precipitate biotinylated proteins, according to the protocol supplied by Pierce, to form an avidin-agarose precipitate. Another aliquot of the yeast cells was lysed and mixed with Concanavalin A-Sepharose (i.e., Con A-Sepharose; available from Pharmacia Biotech Inc., Piscataway, N.J.) to precipitate all of the glycoproteins using standard techniques (see, for example, Franzusoff et al., pp. 2695-2702, 1989, *EMBO J.*, vol. 8), thereby forming a Con A-sepharose precipitate. Both the avidin-agarose precipitate and the Con A-sepharose precipitate were washed, digested with Endoglycosidase H, submitted to immunoblot analysis, and compared to known cell surface and intracellular proteins. The Con A-sepharose precipitate represented essentially all glycoproteins (both intracellular and cell-surface) capable of binding to Con A, whereas the avidin-agarose precipitate represented only proteins that were present on the cell surface and, as such, were capable of being biotinylated. The immunoblots showed that at least a fraction of the total amount of gp120, α/gp120, and gp41 produced was present on the cell surface of *Saccharomyces cerevisiae* GPY60:pα/env.

Example 2

This example demonstrates the ability of a truncated form of *Saccharomyces cerevisiae* Kex2 endoprotease to cleave HIV-1 gp160 in vitro. As such, this example illustrates the potential to use either the in vitro system or yeast strains expressing Kex2 and gp160 to identify drugs that inhibit gp160-cleaving dibasic amino acid processing endoproteases.

Secreted soluble Kex2 protease of *Saccharomyces cerevisiae* (ssKex2), an active dibasic amino acid processing endoprotease lacking the transmembrane domain and carboxyl-terminal tail of the native enzyme, was prepared in a manner similar to that described in Brenner et al., 1992, *Proc. Natl. Acad. Sci.,* ibid. The yield of ssKex2 was about 0.2 to about 0.5 milligram (mg) of protein per liter of culture medium. The proteolytic activity of ssKex2 was determined by quantitating the ability of the enzyme to cleave fluorigenic peptide substrates, such as Boc-Gln-Arg-Arg-MCA as described in Brenner et al., 1992, *Proc. Natl. Acad. Sci.,* ibid.

Radiolabeled HIV-$1_{SF2}$ gp160 precursor protein was prepared by culturing *Saccharomyces cerevisiae* GPY60-:pα/env (prepared as described in Example 1) in the presence of radiolabeled methionine and cysteine, and α/gp160 expression was induced as in Example 1. Radiolabeled yeast spheroplasts were detergent-solubilized at about 4° C. in RIPA buffer (1% TX-100, 0.5% deoxycholate, and 0.1% sodium dodecyl sulfate (SDS) in phosphate-buffered saline (8 grams (g) NaCl, 0.2 g KCl, 1.44 g $Na_2HPO_4$, 0.24 g $KH_2PO_4$, per liter of water, pH 7.4)) to retain quasi-native membrane protein conformation. α/gp160 precursors were immunoprecipitated from the spheroplast lysate using α-factor antisera or Con A-sepharose (see Example 1).

Samples of the immunoprecipitated α/gp160 precursors were incubated with either (a) no addition; (b) ssKex2, (c) ssKex2 and the calcium chelator ethylene glycol-bis(β-aminoethylether, or EGTA (note that ssKex2 is a calcium-dependent enzyme). All samples were incubated under conditions similar to those described in Brenner et al., 1992, *Proc. Natl. Acad. Sci.,* ibid. Briefly, the incubations were conducted for about 30 minutes at about 37° C. in a buffer containing 200 mM bis-Tris-Cl, pH. 7.0, 1 mM calcium chloride, and 0.01% Triton-X-100. The incubations were stopped by heating in about 0.5% SDS. Each sample was then treated with Endoglycosidase H, immunoprecipitated with anti-gp120 antisera, and analyzed by polyacrylamide gel electrophoresis as referenced in Example 1.

Analysis of the immunoprecipitated α/gp160 precursor sample (i.e., sample a) that was not exposed to ssKex2 treatment indicated that a fraction of the α-gp160 precursors had been cleaved in vivo into α/gp120 prior to ssKex2 treatment. Treatment of α/gp160 precursors by ssKex2 in vitro (sample b) led to an about 2 to about 2.5 fold enrichment in α/gp120 and gp120 products compared to the amount of cleaved protein in sample a. The in vitro cleavage was shown to be essentially blocked by EGTA (sample c). As such, these results demonstrate that yeast Kex2 enzyme can effect the cleavage of gp160 into gp120.

Example 3

This example describes the production of a preferred Kex2 endoprotease-deficient yeast strain of the present invention, namely a Kex2-deficient *Saccharomyces cerevisiae* strain that is also defective in the production of a soluble vacuole protease. Such a strain can be used to identify a cellular dibasic amino acid processing endoprotease gene and/or be engineered to produce a cellular dibasic amino acid processing endoprotease.

*Saccharomyces cerevisiae* GPY60, the Matα pep4-::URA3 prb leu2 his4 ura3 trp1 strain described in Example 1, has a disrupted PEP4 gene (i.e., pep4::URA3) and a mutant PRB gene and, as such, does not produce proteinase A or B. The KEX2 gene of GPY60 was disrupted by replacing the functional KEX2 gene with a DNA fragment in which the KEX2 gene is interrupted by a TRP1 gene in a manner analogous to that described by Fuller et al., 1989, *Science*, ibid.). The resultant Kex2 endoprotease-deficient strain, called *Saccharomyces cerevisiae* kex2Δ, has the genotype pep4-::URA3 kex2::TRP1 prb leu2 his4 ura3 trp1.

Example 4

This example demonstrates that HIV-1 gp160 precursor envelope protein can be expressed but not processed (i.e., cleaved) by a Kex2 endoprotease-deficient yeast strain, thereby confirming that gp160 cleavage in yeast is dependent upon Kex2 endoprotease.

*Saccharomyces cerevisiae* kex2Δ, produced as described in Example 3, was transformed with recombinant molecule pα/env, produced as described in Example 1, to produce *Saccharomyces cerevisiae* kex2Δ-:pα/env. The transformed Kex2 endoprotease-deficient strain was cultured and tested by immunoprecipitation and immunoblot techniques for the ability to produce and cleave α/gp160 using methods similar to those described in Example 1. Although *Saccharomyces cerevisiae* kex2Δ:pα/env was able to produce α/gp160, the Kex2 endoprotease-deficient strain did not produce α/gp120, gp120, or gp41. This result affirms that Kex2 is the yeast enzyme responsible for the cleavage of the gp160 precursor envelope protein.

Example 5

This example demonstrates the usefulness of Kex2 endoprotease-deficient *Saccharomyces cerevisiae* strains and α-factor clearing zone (halo) assays to screen for a gene encoding a human CD4+ T-lymphocyte cellular dibasic amino acid processing endoprotease that is responsible for cleavage of gp160 in HIV-1-infected CD4+ T-lymphocytes.

Human CD4+ T-lymphocyte complementary DNA (cDNA) fragments are produced and restriction endonuclease site-containing linkers are ligated to the cDNA fragments according to the protocols described in Sambrook et al., ibid. The resultant mixture of linkered cDNA fragments is then ligated into yeast expression shuttle vector pEMBLyex4 (see, for example, Balari et al., pp. 27–32, 1985, Gene, vol. 35) such that expression of the linkered cDNA fragments is controlled by CYC1/GAL promoter/enhancer and CYC1 terminator sequences present on the vector. The ligation reaction leads to the formation of a yeast expression library of cDNA recombinant molecules. The yeast expression library is amplified in *Escherichia coli*. After amplification, the library is recovered and transformed into a *Saccharomyces cerevisiae* kex2Δ strain by lithium acetate-mediated transfection, resulting in from about $10^5$ to about $10^6$ transformants per microgram (μg) of recombinant molecules.

*Saccharomyces cerevisiae* kex2Δ strains expressing a human CD4+ T-lymphocyte dibasic amino acid processing endoprotease are identified using the α-factor zone clearing or "halo" assay. As heretofore disclosed, when grown on a lawn of *Saccharomyces cerevisiae* microorganisms of the opposite mating type, *Saccharomyces cerevisiae* kex2Δ strains are essentially not able to form a clearing zone, or halo, whereas similar strains expressing Kex2 endoprotease do form halos. *Saccharomyces cerevisiae* kex2Δ strains that are able to produce a heterologous functional dibasic amino acid processing endoprotease, such as a human CD4+ T-lymphocyte dibasic amino acid processing endoprotease (denoted human TKX or hTKX) due to the strain being transformed by the appropriate recombinant molecule, are also capable of producing mature α-factor pheromones and, hence, are capable of forming halos when grown on the appropriate yeast lawn in the α-factor zone clearing assay.

The zone clearing assay is conducted in a manner similar to that described by Julius et al., 1984, *Cell*, ibid. Briefly, from about $10^6$ to about $10^7$ *Saccharomyces cerevisiae* MATa sst2 cells (which are about 100 to about 300 times more susceptible to α-factor than are normal cells) are spread onto plates containing solid growth medium that enables the maintenance of cDNA recombinant molecules in the library-transformed *Saccharomyces cerevisiae* kex2Δ cells. An appropriate number of colonies of the library-transformed *Saccharomyces cerevisiae* kex2Δ strain are replica-plated onto the lawns in order to represent the entire library more than three times. The plates are incubated as described by Julius et al., 1984, *Cell*, ibid. until halos form around control colonies (e.g., *Saccharomyces cerevisiae* GPY60). Transformed *Saccharomyces cerevisiae* kex2Δ strains that restore the halo phenotype are isolated. cDNA recombinant molecules are recovered from the isolated strains, retransformed into *Saccharomyces cerevisiae* kex2Δ strains, and rescreened using the α-factor clearing zone assay. Recombinant molecules that encode a functional CD4+ T-lymphocyte dibasic amino acid processing endoprotease are purified and the gene encoding human TKX (denoted the human TKX or hTKX gene) is subjected to further analysis, such as sequencing and comparison with other dibasic amino acid processing endoprotease and yeast KEX2 genes.

Example 6

This example demonstrates that expression of a human CD4+ T-lymphocyte dibasic amino acid processing endoprotease gene in a Kex2 endoprotease-deficient *Saccharomyces cerevisiae* strain capable of expressing an HIV-1 gp160 precursor protein results in cleavage of the gp160 into gp120 and gp41. This example also demonstrates that at least some of the processed gp120 and gp41 glycoproteins are expressed on the yeast cell surface.

The human CD4+ T-lymphocyte dibasic amino acid processing endoprotease gene (hTKX gene), which can be isolated as described in Example 5, is operatively linked to *Saccharomyces cerevisiae* ADH2/GAPDH promoter and α-factor transcription termination sequences in a manner analogous to the ligation of the α/env gene to such transcription control sequences (see Example 1). The hTKX gene and transcription control sequences-containing fragment is inserted into recombinant molecule pα/env (described in Example 1) in such a manner that both the hTKX and α/env genes are expressed when the resultant plasmid, denoted pα/env-hTKX, is transformed into yeast strain *Saccharomyces cerevisiae* kex2Δ. The transformed strain, denoted *Saccharomyces cerevisiae* kex2Δ:pα/env-hTKX, is cultured and α/env and hTKX expression induced as described in Example 1. The ability of the expressed human TKX endoprotease to cleave gp160 into gp120 and gp41 is demonstrated using immunoprecipitation and immunoblot techniques similar to those cited in Example 1. The ability of *Saccharomyces cerevisiae* kex2Δ:pα/env-hTKX to express gp120 and gp41 on its cell surface is demonstrated using a cell surface biotinylation assay similar to that described in Example 1.

Example 7

This example demonstrates that a secreted soluble form of CD4+ T-lymphocyte dibasic amino acid processing endoprotease is capable of cleaving both an HIV-1 gp160 precursor protein and an α-factor precursor protein in vitro. This truncated endoprotease is a component of in vitro assays to identify compounds that exhibit high selectivity in their ability to inhibit cleavage of gp160 and, as such, reduce HIV infectivity. The endoprotease is also useful in structure-function studies to design better inhibitory compounds.

A modified human CD4+ T-lymphocyte dibasic amino acid processing endoprotease, denoted sshTKX, that lacks the transmembrane domain and carboxyl-terminal tail and, as such is a soluble protein that is secreted by the cell that produces it, is produced in the following manner. The gene encoding sshTKX is produced by truncating the hTKX gene referenced in Example 5 to remove the domains that prevent secretion of the full-length protein in a manner analogous to that described in Brenner et al., 1992, *Proc. Natl. Acad. Sci.*, ibid. for construction of the gene encoding the yeast ssKex2 protein. The sshTKX gene is inserted into a yeast expression shuttle vector to form recombinant molecule psshTKX such that the sshTKX gene is operatively linked to *Saccharomyces cerevisiae* ADH2-/GAPDH promoter and α-factor transcription termination sequences. psshTKX is transformed into *Saccharomyces cerevisiae* kex2Δ to form *Saccharomyces cerevisiae* kex2Δ:psshTKX. The transformed strain is cultured, sshTKX expression induced, and sshTKX recovered in a manner similar to that carried out for the recovery of ssKex2 cited in Example 2.

Radiolabeled α/HIV-1$_{SF2}$ gp160 precursor protein, prepared as described in Example 2, is incubated in the presence and absence of sshTKX under conditions similar to those described in Example 2 but optimized as necessary for hTKX proteolytic activity. Each reaction is stopped, treated with Endoglycosidase H, immunoprecipitated with anti-gp120 antisera, and submitted to polyacrylamide gel electrophoresis as described in Example 2. Such studies show that sshTKX endoprotease is capable of effecting the cleavage of gp160 to gp120 in vitro.

Analysis of in vitro proteolysis reactions containing sshTKX and in vitro-translated radiolabeled α-factor precursor protein, produced as described in Franzusoff et al., 1991, *J. Cell. Biol.*, ibid., indicates that the sshTKX endoprotease is also capable of cleaving α-factor precursor proteins into α-factor mating pheromones.

Example 8

This example demonstrates the utility of an in vivo yeast-based assay to identify inhibitors of HIV-1 infection. The assay described in this Example uses a yeast strain which need not be transformed with a heterologous gene and monitors the ability of putative inhibitory compounds to block cleavage of α-factor precursor proteins.

*Saccharomyces cerevisiae* GPY60, a typical laboratory haploid strain cited in Example 1, is cultured according to standard techniques (see, for example, Guthrie et al. (eds.), ibid.) and divided into samples that are placed, for example, in microtiter dish wells. Each sample is incubated with about 300 μM, 100 μM, 10 μM, 1 μM, 300 nM, 100 nM, 10 nM, 1 nM, or none of one of the following peptides: Boc-Arg-Glu-Lys-Arg-MCA (derivatized SEQ ID NO: 5) or Boc-Gln-Arg-Arg-MCA (available from Peninsula Laboratories, Inc., Belmont, Calif., or Peptides International, Inc., Louisville, Ky.) under culturing conditions for about 12 hours. After culturing, an aliquot of the medium of each cultured sample is recovered and submitted to the α-factor zone clearing assay by spotting the aliquot onto a lawn of about $10^6$ *Saccharomyces cerevisiae* MATa sst2 cells and incubating the plates as described in Example 5 until a halo forms around the control sample (no peptide added) and around spots containing known amounts of *Saccharomyces cerevisiae* α-factor mating pheromone (for example, amounts ranging from about 1 to about 100 picomoles). The ability of each dose of each peptide to inhibit Kex2 activity and, thus, be a potential inhibitor of gp160 cleavage, is determined by measuring the size of the halo formed around each spotted aliquot and comparing the diameter to the halo formed by the known amounts of α-factor mating pheromone spotted onto the lawn. Peptides that inhibit maturation of α-factor mating pheromones at suitable doses can be submitted to one or more of the assays described in Examples 9–12 and can subsequently be tested for their ability to inhibit syncytium and/or infectious virus formation by HIV-1-infected CD4+ T-lymphocytes, using, for example, the methods described by Sodroski et al., pp. 470–474, 1986, *Nature*, vol. 322.

Example 9

This example demonstrates the ability to identify inhibitors of HIV-1 infection using a Kex2 endoprotease-deficient *Saccharomyces cerevisiae* strain transformed with a gene encoding the human CD4+ T-lymphocyte dibasic amino acid processing endoprotease that can cleave HIV-1 gp160 precursor proteins.

*Saccharomyces cerevisiae* kex2Δ:phTKX, a Kex2 endoprotease-deficient *Saccharomyces cerevisiae* strain capable of producing human CD4+ T-lymphocyte dibasic amino acid processing endoprotease, is produced by transforming *Saccharomyces cerevisiae* kex2Δ (produced as described in Example 3) with recombinant molecule phTKX. Recombinant molecule phTKX is a yeast expression shuttle vector containing the hTKX gene, produced as described in Example 5, operatively linked to *Saccharomyces cerevisiae* ADH2/GAPDH promoter and α-factor transcription termination sequences. Recombinant molecule phTKX is produced in a manner similar to that described for the production of recombinant molecules pα/env in Example 1 and pα/env-hTKX in Example 6. In order to screen for inhibitors that block HIV-1 infection, *Saccharomyces cerevisiae* kex2α:phTKX is cultured according to standard techniques (see, for example, Guthrie et al. (eds.), ibid.) and divided into samples that are placed, for example, in microtiter dish wells. Each sample is incubated with about 300 μM, 100 μM, 10 μM, 1 μM, 300 nM, 100 nM, 10 nM, 1 nM, or none of one of the following peptides: Boc-Arg-Glu-Lys-Arg-MCA (derivatized SEQ ID NO: 5) or Boc-Gln-Arg-Arg-MCA under culturing conditions for about 12 hours. After culturing, an aliquot of the medium of each cultured sample is recovered and submitted to the α-factor zone clearing assay, as described in Example 8. Peptides that inhibit maturation of α-factor mating pheromones at suitable doses are identified and can be submitted to one or more of the assays described in Examples 10–12 and can subsequently be tested for their ability to inhibit syncytium and/or infectious virus formation by HIV-1-infected CD4+ T-lymphocytes, using, for example, the methods cited in Example 8.

Example 10

This example demonstrates the utility of a yeast based assay to identify inhibitors of HIV-1 infection. The assay uses yeast strains that produce HIV-1 gp160 precursor proteins and that are able to cleave gp160 into gp120.

Either *Saccharomyces cerevisiae* GPY60:pα/env (produced as described in Example 1) or *Saccharomyces cerevisiae* kex2Δ:pα/env-hTKX (produced as described in Example 6) is cultured and divided into samples as described in Example 8. Each sample is incubated with about 300 μM, 100 μM, 10 μM, 1 μM, 300 nM, 100 nM, 10 nM, 1 nM, or none of one of the following peptides: Boc-Arg-Glu-Lys-Arg-MCA (derivatized SEQ ID NO: 5) or Boc-Gln-Arg-Arg-MCA under culturing conditions for about 12 hours. Putative inhibitory compounds can be pre-incubated with the yeast strain prior to induction of gp160 expression. After culturing, cells from each sample are lysed and submitted to immunoprecipitation and/or immunoblot analysis to measure α/gp160, α/gp120, gp120, and gp41 production, using the techniques described in Example 1. Peptides that inhibit cleavage of gp160 to gp120 at suitable doses are identified and can be further tested for their ability to inhibit syncytium and/or infectious virus formation by HIV-1-infected CD4+ T-lymphocytes, using, for example, the methods cited in Example 8.

Example 11

This example demonstrates the ability to use *Saccharomyces cerevisiae* ssKex2 endoprotease in vitro to identify inhibitors of HIV-1 infection.

Samples containing from about 0.1 μg to about 1.0 μg of partially purified *Saccharomyces cerevisiae* ssKex2 endoprotease, produced as described in Example 2, and from about 0.1 μg to about 1.0 μg of in vitro-translated radiolabeled α-factor precursor protein, produced as described in Example 7, were incubated with about 0, 0.1, 0.25, 0.5, 0.75, and 1 mM of the fluorigenic peptide Boc-Gln-Arg-Arg-MCA under conditions similar to the ssKex2 assays described in Example 2, such that in the absence of inhibitor, cleavage did occur. Addition of 0.5, 0.75, or 1.0 mM of the peptide inhibited cleavage by about 75 percent, whereas addition of 0.25 or 0.1 mM of the peptide inhibited cleavage by, respectively, about 65 percent and about 40 percent. A non-specific inhibitor, such as substance P peptide (Arg-Pro-Lys-Gln-Gln-Phe-Phe-Gly-Leu-Met) (SEQ ID NO: 6) did not substantially inhibit cleavage by ssKex2. These results indicate that Boc-Gln-Arg-Arg-MCA, which is a competitive substrate inhibitor, can inhibit ssKex2 activity. Testing of from about 0.5 to about 1.0 mM of the peptide in one or more of the assays described in Examples 8–10 and in syncytium and/or infectious virus formation assays, such as those cited in Example 8, can better characterize the efficacy of the peptide as an antiviral agent.

Example 12

This example demonstrates the ability to use truncated versions of the yeast Kex2 and human TKX endoproteases in in vitro assays to identify inhibitors of HIV-1 infection.

Either *Saccharomyces cerevisiae* ssKex2 endoprotease, produced as described in Example 2, or human sshTKX endoprotease, produced as described in Example 7 is mixed with radiolabeled α/HIV-1$_{SF2}$ gp160 precursor protein, produced as described in Example 2 at a ratio of protease to protein that is sufficient to effect cleavage of at least a portion of gp160 by the respective endoprotease. Each mixture is divided into samples, and each sample is incubated with about 300 μM, 100 μM, 10 μM, 1 μM, 300 nM, 100 nM, 10 nM, 1 nM, or none of one of the following peptides: Boc-Arg-Glu-Lys-Arg-MCA (derivatized SEQ ID NO: 5) or Boc-Gln-Arg-Arg-MCA for about 1 to about 2 hours under conditions that in the absence of a potential inhibitor would effect cleavage (see, Examples 2 and 7, respectively, for the yeast and human endoprotease conditions). The extent of cleavage in each sample is analyzed by immunoprecipitation followed by polyacrylamide gel electrophoresis as described in Examples 2 and 7. Peptides that inhibit cleavage of gp160 to gp120 at suitable doses can be submitted to one or more of the assays described in Examples 8–10 and can subsequently be tested for their ability to inhibit syncytium and/or infectious virus formation by HIV-1-infected CD4+ T-lymphocytes, using, for example, the methods cited in Example 8.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to identify a compound that inhibits proteolytic cleavage by a dibasic amino acid processing endoprotease, said method comprising:
   (a) contacting a yeast strain containing a precursor protein having a dibasic amino acid processing site with a putative inhibitory compound under conditions in which, in the absence of said compound, said yeast strain is capable of effecting cleavage of said precursor protein into cleavage products; and
   (b) assaying for production of at least one of said cleavage products, wherein production of a reduced amount of said at least one of said cleavage products in the presence of said putative inhibitory compound compared to in the absence of said putative inhibitory compound indicates that said compound is able to inhibit proteolytic cleavage by said endoprotease.

2. The method of claim 1, wherein said yeast strain is of a genus selected from the group consisting of Saccharomyces, Pichia, Hansenula, Schizosaccharomyces, Kluyveromyces, Yarrowia and Candida.

3. The method of claim 1, wherein said yeast strain is of the species *Saccharomyces cerevisiae*.

4. The method of claim 1, wherein said cleavage of said precursor protein in step (a) is accomplished by a yeast Kex2 endoprotease or functional equivalent thereof, said functional equivalent being capable of cleaving a yeast α-factor precursor protein in an α-factor zone clearing assay.

5. The method of claim 1, wherein said cleavage of said precursor protein in step (a) is accomplished by a dibasic amino acid processing endoprotease heterologous to said yeast strain, said heterologous endoprotease being produced by said yeast strain.

6. The method of claim 5, wherein said yeast strain is Kex2 endoprotease-deficient.

7. The method of claim 6, wherein said yeast strain is deficient in at least one soluble vacuolar protease.

8. The method of claim 1, wherein said yeast strain comprises a Kex2 endoprotease-deficient *Saccharomyces cerevisiae* strain capable of producing a heterologous dibasic amino acid processing endoprotease.

9. The method of claim 8, wherein said yeast strain comprises *Saccharomyces cerevisiae* kex2Δ.

10. The method of claim 1, wherein said endoprotease comprises a cellular endoprotease selected from the group consisting of animal endoproteases and plant endoproteases.

11. The method of claim 1, wherein said endoprotease comprises a cellular endoprotease selected from the group consisting of mammalian, avian, fish and insect cellular endoproteases.

12. The method of claim 1, wherein said endoprotease is selected from the group consisting of human, simian, feline, canine, bovine and rodent cellular endoproteases.

13. The method of claim 1, wherein said endoprotease is derived from a cell type that is capable of producing infectious virus upon infection by an enveloped virus.

14. The method of claim 1, wherein said endoprotease is capable of effecting cleavage of at least one envelope protein of an enveloped virus.

15. The method of claim 1, wherein said endoprotease is derived from a cell type that is capable of producing infectious virus upon infection by a human immunodeficiency virus.

16. The method of claim 1, wherein said endoprotease is capable of effecting cleavage of human immunodeficiency virus gp160.

17. The method of claim 1, wherein said endoprotease comprises a human CD4+ T-lymphocyte dibasic amino acid processing endoprotease.

18. The method of claim 1, wherein said precursor protein comprises a yeast precursor protein.

19. The method of claim 1, wherein said precursor protein is selected from the group consisting of yeast α-factor precursor proteins and yeast killer toxin precursor proteins.

20. The method of claim 1, wherein said precursor protein comprises a precursor protein heterologous to said yeast strain, said yeast strain being capable of producing said heterologous precursor protein.

21. The method of claim 1, wherein inhibition of said cleavage of said precursor protein into at least one cleavage protein reduces the infectivity of an infectious agent.

22. The method of claim 1, wherein said precursor protein comprises a polyprotein.

23. The method of claim 1, wherein said precursor protein is selected from the group consisting of viral, bacterial, fungal, plant and animal precursor proteins.

24. The method of claim 1, wherein said precursor protein comprises at least one precursor viral envelope protein.

25. The method of claim 1, wherein said precursor protein is a precursor envelope protein of a virus selected from the group consisting of retroviruses, herpes viruses, hepadnaviruses, pox viruses, orthomyxoviruses, paramyxoviruses, rhabdoviruses, togaviruses, arena viruses, bunyaviruses and coronaviruses.

26. The method of claim 1, wherein said precursor protein is selected from the group consisting of a precursor retrovirus envelope protein, a precursor hepatitis virus envelope protein, and a precursor herpes virus envelope protein.

27. The method of claim 1, wherein said precursor protein comprises a precursor lentivirus envelope protein or a precursor lymphotrophic virus envelope protein.

28. The method of claim 1, wherein said precursor protein is selected from the group consisting of HIV-1 gp160, HIV-2 gp160, HTLV-I gp69, HTLV-II gp69, and functional equivalents thereof, said functional equivalents being capable, upon cleavage by a dibasic amino acid processing endoprotease, of functioning as viral envelope proteins.

29. The method of claim 1, wherein said precursor protein further comprises at least one protein segment that enhances correct processing of said precursor protein in the Golgi apparatus of said yeast strain.

30. The method of claim 29, wherein said segment enhances export of said precursor protein through the secretory pathway of said yeast strain.

31. The method of claim 29, wherein said segment is selected from the group consisting of leader sequences, dibasic amino acid processing sites, and combinations thereof.

32. The method of claim 29, wherein said segment comprises a yeast α-factor mating pheromone leader sequence joined to a yeast α-factor dibasic amino acid processing site.

33. The method of claim 1, wherein said yeast strain comprises a Kex2 endoprotease-deficient *Saccharomyces cerevisiae* strain capable of producing a precursor envelope protein selected from the group consisting of HIV-1 gp160, HIV-2 gp160, HTLV-I gp69, HTLV-II gp69, and functional equivalents thereof, said functional equivalents being capable, upon cleavage by a dibasic amino acid processing endoprotease, of functioning as viral envelope proteins, and capable of producing a human CD4+ T-lymphocyte dibasic amino acid processing endoprotease capable of cleaving said precursor envelope protein.

34. The method of claim 1, wherein said step of assaying comprises testing for dibasic amino acid processing endoprotease activity by an α-factor zone clearing assay.

35. The method of claim 1, wherein said step of assaying comprises testing for said cleavage of said precursor protein by measuring the amount of cleavage protein produced from said precursor protein.

36. The method of claim 1, wherein said inhibitory compound is capable of being endocytosed.

37. The method of claim 1, wherein said inhibitory compound is selected from the group consisting of peptides, mimetopes, and mixtures thereof.

38. The method of claim 1, wherein said inhibitory compound is capable of chemically inactivating said endoprotease.

39. A method to identify an inhibitory compound that reduces the infectivity of an infectious agent, comprising:
   (a) contacting a yeast strain containing a precursor protein having a dibasic amino acid processing site with a putative inhibitory compound under conditions in which, in the absence of the compound, said yeast strain is capable of effecting cleavage of said precursor protein into cleavage products; and
   (b) assaying for production of said cleavage products, wherein production of a reduced amount of said cleavage products in the presence of said putative inhibitory compound compared to in the absence of said putative inhibitory compound indicates that said compound is able to inhibit proteolytic cleavage by said endoprotease, the ability of said compound to inhibit said cleavage being indicative of the ability of said compound to reduce the spread of said infectious agent in an organism infected by said infectious agent.

40. The method of claim 39, wherein said yeast strain is capable of producing a precursor protein of said infectious agent.

41. The method of claim 39, wherein said yeast strain is a Kex2 endoprotease-deficient yeast strain capable of producing a dibasic amino acid processing endoprotease, said endoprotease being derived from a cell type capable of being infected by said infectious agent.

42. The method of claim 39, wherein said infectious agent comprises an enveloped virus.

43. A test kit to identify a compound capable of inhibiting a dibasic amino acid processing endoprotease, said kit comprising a yeast strain capable of producing a precursor protein selected from the group consisting of yeast and heterologous precursor proteins, said yeast strain being capable of effecting cleavage of said precursor protein into cleavage products, and a means for determining the extent of cleavage by said yeast strain in the presence of a putative inhibitory compound, said means for determining comprising means for assaying for production of said cleavage products, wherein production of a reduced amount of said cleavage products in the presence of said putative inhibitory compound compared to in the absence of said putative inhibitory compound indicates that said compound is able to inhibit proteolytic cleavage by said endoprotease.

44. The kit of claim 43, wherein said yeast strain comprises a Kex2 endoprotease-deficient yeast strain capable of producing a heterologous dibasic amino acid processing endoprotease.

45. The kit of claim 43, wherein inhibition of said cleavage of said precursor protein into at least one cleavage protein reduces the infectivity of an infectious agent.

46. The kit of claim 43, wherein said means for determining comprises an α-factor zone clearing assay.

47. A method to identify a compound capable of inhibiting an animal or plant dibasic amino acid processing endoprotease, said method comprising:
   (a) contacting a putative inhibitory compound with a secreted soluble dibasic amino acid processing endoprotease protein fragment in the presence of a precursor protein having a dibasic amino acid processing site under conditions in which, in the absence of said compound, said protein fragment is capable of effecting cleavage of said precursor protein into cleavage products; and
   (b) assaying for production of said cleavage products, wherein production of a reduced amount of said cleavage products in the presence of said putative inhibitory compound compared to in the absence of said putative inhibitory compound indicates that said compound is able to inhibit proteolytic cleavage by said endoprotease.

48. The method of claim 47, wherein said protein fragment comprises a secreted soluble yeast Kex2 protein fragment.

49. The method of claim 47, wherein said protein fragment comprises a soluble secreted mammalian dibasic amino acid processing endoprotease protein fragment.

* * * * *